(12) United States Patent
Carr-Brendel et al.

(10) Patent No.: US 7,364,592 B2
(45) Date of Patent: Apr. 29, 2008

(54) BIOINTERFACE MEMBRANE WITH MACRO-AND MICRO-ARCHITECTURE

(75) Inventors: Victoria Carr-Brendel, San Diego, CA (US); Peter C. Simpson, Del Mar, CA (US); James H. Brauker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 296 days.

(21) Appl. No.: 11/055,779

(22) Filed: Feb. 9, 2005

(65) Prior Publication Data

US 2005/0251083 A1 Nov. 10, 2005

Related U.S. Application Data

(60) Provisional application No. 60/544,722, filed on Feb. 12, 2004.

(51) Int. Cl.
*A61F 2/02* (2006.01)
(52) U.S. Cl. ..................... 623/23.76; 424/424
(58) Field of Classification Search ............. 623/23.76; 424/424
See application file for complete search history.

(56) References Cited

U.S. PATENT DOCUMENTS

| | | | |
|---|---|---|---|
| 3,929,971 A | 12/1975 | Roy | |
| 4,076,656 A | 2/1978 | White et al. | |
| 4,625,730 A | 12/1986 | Fountain et al. | |
| 4,686,044 A | 8/1987 | Behnke et al. | |
| 4,702,857 A | 10/1987 | Gosselink | |
| 4,703,756 A | 11/1987 | Gough et al. | |
| 4,757,022 A | 7/1988 | Shults et al. | |
| 4,803,243 A | 2/1989 | Fujimoto et al. | |
| 4,889,744 A | 12/1989 | Quaid | |
| 4,940,065 A | 7/1990 | Tanagho et al. | |
| 4,994,167 A | 2/1991 | Shults et al. | |
| 5,002,572 A | 3/1991 | Picha | |
| 5,007,929 A | 4/1991 | Quaid | |
| 5,113,871 A | 5/1992 | Viljanto et al. | |
| 5,130,231 A * | 7/1992 | Kennedy et al. ............... | 435/4 |
| 5,171,689 A | 12/1992 | Kawaguri et al. | |
| 5,207,218 A | 5/1993 | Carpentier et al. | |
| 5,271,736 A | 12/1993 | Picha | |
| 5,310,469 A | 5/1994 | Cunningham et al. | |
| 5,314,471 A | 5/1994 | Brauker et al. | |
| 5,326,356 A | 7/1994 | Della Valle et al. | |
| 5,344,454 A | 9/1994 | Clarke et al. | |
| 5,348,788 A | 9/1994 | White | |
| 5,453,278 A | 9/1995 | Chan et al. | |
| 5,458,631 A | 10/1995 | Xavier | |
| 5,545,220 A | 8/1996 | Andrews et al. | |
| 5,545,223 A | 8/1996 | Neuenfeldt et al. | |
| 5,549,675 A | 8/1996 | Neuenfeldt et al. | |
| 5,564,439 A | 10/1996 | Picha | |
| 5,569,462 A | 10/1996 | Martinson et al. | |
| 5,584,876 A | 12/1996 | Bruchman et al. | |
| 5,593,440 A | 1/1997 | Brauker et al. | |
| 5,624,537 A | 4/1997 | Turner et al. | |
| 5,653,756 A | 8/1997 | Clarke et al. | |
| 5,658,330 A | 8/1997 | Carlisle et al. | |
| 5,681,572 A | 10/1997 | Seare | |
| 5,706,807 A | 1/1998 | Picha | |
| 5,713,888 A | 2/1998 | Neuenfeldt et al. | |
| 5,733,336 A | 3/1998 | Neuenfeldt et al. | |
| 5,741,330 A | 4/1998 | Brauker et al. | |
| 5,782,880 A | 7/1998 | Lahtinen et al. | |
| 5,782,912 A | 7/1998 | Brauker et al. | |
| 5,787,900 A | 8/1998 | Butler et al. | |
| 5,791,344 A | 8/1998 | Schulman et al. | |
| 5,798,065 A | 8/1998 | Picha | |
| 5,800,529 A | 9/1998 | Brauker et al. | |

(Continued)

FOREIGN PATENT DOCUMENTS

WO WO 92/07525 5/1992

(Continued)

OTHER PUBLICATIONS

The term "nominal", Merriam-Webster Online Dictionary—at the web—http://www.m-w.com, p. 1.*

(Continued)

*Primary Examiner*—Irene Marx
*Assistant Examiner*—Satyendra K Singh
(74) *Attorney, Agent, or Firm*—Knobbe Martens Olson & Bear LLP

(57) ABSTRACT

Disclosed herein are biointerface membranes including a macro-architecture and a micro-architecture co-continuous with and bonded to and/or located within at least a portion of the macro-architecture. The macro- and micro-architectures work together to manage and manipulate the high-level tissue organization and the low-level cellular organization of the foreign body response in vivo, thereby increasing neovascularization close to a device-tissue interface, interfering with barrier cell layer formation, and providing good tissue anchoring, while reducing the effects of motion artifact, and disrupting the organization and/or contracture of the FBC. The biointerface membranes of the preferred embodiments can be utilized with implantable devices such as devices for the detection of analyte concentrations in a biological sample (for example, from a body), cell transplantation devices, drug delivery devices, electrical signal delivering or measuring devices, and/or combinations thereof.

11 Claims, 8 Drawing Sheets

U.S. PATENT DOCUMENTS

| | | | |
|---|---|---|---|
| 5,807,406 | A | 9/1998 | Brauker et al. |
| 5,820,589 | A | 10/1998 | Torgerson et al. |
| 5,840,240 | A | 11/1998 | Stenoien et al. |
| 5,913,998 | A | 6/1999 | Butler et al. |
| 5,964,745 | A | 10/1999 | Lyles et al. |
| 5,964,804 | A | 10/1999 | Brauker et al. |
| 5,972,369 | A | 10/1999 | Roorda et al. |
| 5,987,352 | A | 11/1999 | Klein et al. |
| 6,001,067 | A | 12/1999 | Shults et al. |
| 6,015,572 | A | 1/2000 | Lin et al. |
| 6,055,456 | A | 4/2000 | Gerber |
| 6,083,523 | A | 7/2000 | Dionne et al. |
| 6,157,860 | A | 12/2000 | Hauger et al. |
| 6,175,767 | B1 | 1/2001 | Doyle |
| 6,231,879 | B1 | 5/2001 | Li et al. |
| 6,309,384 | B1 | 10/2001 | Harrington et al. |
| 6,330,464 | B1 | 12/2001 | Colvin, Jr. et al. |
| 6,368,274 | B1 | 4/2002 | Van Antwerp et al. |
| 6,372,244 | B1 | 4/2002 | Antanavich et al. |
| 6,406,066 | B1 | 6/2002 | Uegane |
| 6,447,448 | B1 | 9/2002 | Ishikawa et al. |
| 6,447,542 | B1 | 9/2002 | Weadock |
| 6,454,710 | B1 | 9/2002 | Ballerstadt et al. |
| 6,459,917 | B1 | 10/2002 | Gowda et al. |
| 6,471,689 | B1 | 10/2002 | Joseph et al. |
| 6,484,046 | B1 | 11/2002 | Say et al. |
| 6,512,939 | B1 | 1/2003 | Colvin et al. |
| 6,558,321 | B1 | 5/2003 | Burd et al. |
| 6,579,690 | B1 | 6/2003 | Bonnecasze et al. |
| 6,702,857 | B2 | 3/2004 | Brauker et al. |
| 6,741,877 | B1 | 5/2004 | Shults et al. |
| 6,862,465 | B2 | 3/2005 | Shults et al. |
| 2002/0151796 | A1 | 10/2002 | Koulik |
| 2003/0032874 | A1 | 2/2003 | Rhodes et al. |
| 2003/0078560 | A1 | 4/2003 | Miller et al. |
| 2003/0190383 | A1 | 10/2003 | Kim |
| 2004/0045879 | A1 | 3/2004 | Shults et al. |
| 2004/0186362 | A1 | 9/2004 | Brauker et al. |
| 2004/0199059 | A1 | 10/2004 | Brauker et al. |
| 2005/0027180 | A1 | 2/2005 | Goode et al. |
| 2005/0027181 | A1 | 2/2005 | Goode et al. |
| 2005/0027462 | A1 | 2/2005 | Goode et al. |
| 2005/0027463 | A1 | 2/2005 | Goode et al. |
| 2005/0031689 | A1 | 2/2005 | Shults et al. |
| 2005/0033132 | A1 | 2/2005 | Shults et al. |
| 2005/0043598 | A1 | 2/2005 | Goode et al. |
| 2005/0051427 | A1 | 3/2005 | Brauker et al. |
| 2005/0051440 | A1 | 3/2005 | Simpson et al. |
| 2005/0054909 | A1 | 3/2005 | Petisce et al. |
| 2005/0056552 | A1 | 3/2005 | Simpson et al. |
| 2005/0090607 | A1 | 4/2005 | Tapsak et al. |
| 2005/0112169 | A1 | 5/2005 | Brauker et al. |
| 2005/0192557 | A1 | 9/2005 | Brauker et al. |

FOREIGN PATENT DOCUMENTS

| | | |
|---|---|---|
| WO | WO 92/13271 | 8/1992 |
| WO | WO 93/19701 | 10/1993 |
| WO | WO 96/01611 | 1/1996 |
| WO | WO 96/32076 | 10/1996 |
| WO | WO 96/36296 | 11/1996 |
| WO | WO 97/43633 | 11/1997 |
| WO | WO 00/13003 | 3/2000 |
| WO | WO 01/12158 | 2/2001 |
| WO | WO 01/43660 A2 | 6/2001 |

OTHER PUBLICATIONS

Loffler P. et al. Separation and determination of traces of ammonia in air by means of chromatomembrane cells, Fresenius J. Anal. Chem., 1995, 352: 613-614, entire document.*

Pineda L. M. et al. Bone regeneration with resorbable polymeric membranes. III. Effect of poly(L-lactide) membrane pore size on bone healing process in large defects, J. Biomedical Materials Research, 1996, 31: 385-394, entire document.*

Brauker, et al. Sustained expression of high levels of human factor IX from human cells implanted within an immunoisolation device into athymic rodents. Hum Gene Ther 1998, 9, 879-888.

D'Arrigo, et al. Poro -Si based bioreactors for glucose monitoring and drugs production. Proc. of SPIE 2003, 4982, 178-184.

Garg, S.; Schwartz, S.; Edelman, S. Improved Glucose Excursions Using an Implantable Real-Time Continuo Glucose Sensor in Adults with Type I Diabetes. Diabetes Care 2004, 27, 734-738.

Geller, et al. Use of an immunoisolation device for cell transplantation and tumor immunotherapy. Ann NY Acad Sci 1997, 831, 438-451.

Gerritsen, et al. Influence of inflammatory cells and serum on the performance of implantable glucose sensors. J Biomed Mater Res 2001, 54, 69-75.

Gilligan , et al. 1994. Evaluation of a subcutaneous glucose sensor out to 3 months in a dog model. *Diabetes Care*, 17(8):882-887.

Gross, et al. *Performance Evaluation of the Minimed®, Continuous glucose Monitoring System During Patient Home Use*, Diabetes Techn. & Therapeutics, vol. 2, 1, (2000). pp. 49-56.

Klueh, et al. *Use of Vascular Endothelia Cell Growth Factor Gene Transfer to Enhance Implantable Sensor Function* in vivo, Biosensor Function and Vegf-Gene Transfer, 2003. pp. 1072-1086.

Makale, et al. 2003. Tissue window chamber system for validation of implanted oxygen sensors. *Am. J. Physiol. Heart Circ. Physiol.*, 284:H2288-2294.

Miller, A. Human monocyte/macrophage activation and interleukin 1 generation by biomedical po lymers. J Biomed Mater Res 1988, 23, 713-731.

Miller, et al. Generation of IL-1 like activity in response to biomedical polymer implants: a comparison of in vitro and in vivo models. J Biomed Mater Res 1989, 23, 1007-1026.

Miller, et al. In vitr o stimulation of fibroblast activity by factors generated from human monocytes activated by biomedical polymers. Journal of J Biomed Mater Res 1989, 23, 911-930.

Mo ussy, et al. Biomaterials community examines biosensor biocompatibility. Diabetes Technol Ther 2000, 2, 473-477.

Nam, et al. A novel fabrication method of macroporo us biodegradable polymer scaffolds using gas foaming salt as a porogen additive. J Biomed Mater Res 2000, 53, 1-7.

Ratner, B.D. Reducing capsular thickness and enhancing angiogenesis around implant drug release systems. J Control Release 2002, 78, 211-218.

Rhodes, et al. 1994. Prediction of pocket—portable and implantable glucose enzyme electrode performance from combined species permeability and digial simuation analyses *Analytical Chemistry* 66, (9) 1520-1529.

Sanders, et al. *Fibrous Encapsulation of Single Polymer Microfibers Depends on their Vertical Dimension in subcutaneous Tissue*, Polymer Microfibers (2003) pp. 1181-1187.

Sachlos et al. *Making Tissue Engineering Scaffolds Work. Review on the Application of Solid Freeform Fabrication Technology to the Production of Tissue Engineering Scaffolds*, European Cells and Materials vol. 5, 2003 (29-40).

Sieminski, et al. Biomaterial—microvasculature interactions. Biomaterials 2000, 21, 2233-2241.

Tang, et al. Fibrin(ogen) mediates acute inflammatory responses to biomaterials. J Exp Med 1993, 178, 2147-2156.

Tang, et al. Inflammatory responses to biomaterials. Am J Clin Pathol 1995, 103, 466-471.

Tang, et al. Mast cells mediate acute inflammatory responses to implanted biomaterials. Proc Natl Acad Sci U S A 1998, 95, 8841-8846.

Tang, et al. Molecular determinants of acute inflammatory responses to biomaterials. J Clin Invest 1996, 97, 1329-1334.

Tibell, et al. Survival of macroencapsulated allogeneic parathyroid tissue one year after transplantation in nonimmunosuppressed humans. Cell Transplant 2001, 10, 591-9.

Updike et al. 1997. Principles of long -term fully implanted sensors with emphasis on radiotelemtric monitoring of blood glucose from inside a subcutaneous foreign body capsule (FBC). In Fraser, D. M. (Ed.). Biosensors in the Body: Continuous in vivo Monitoring. Chap. 4, pp. 117-137, Hoboken, NJ: John Wiley.

Updike, et al. 2000. A subcutaneous glucose sensor with improved longevity, dynamic range, and stability of calibration. *Diabetes Care*, 23(2):208-214.

Updike, et al. 1982 Implanting the glucose enzyme electrode: Problems, Progress, and alternative solutions, *Diabetes Care*, 5, (3) 207-212.

Ward et al. 2002 . A new amperometric glucose microsensor: In vitro and short-term in vivo evaluation. *Biosensors & Bioelectronics*, 17:181-189.

Wilkins, E.; Atanasov, P. Glucose monitoring: state of the art and future possibilities. Med Eng Phys 1995, 18, 273-288.

Wilson, et al. 1992. Progress toward the development of an implantable sensor for glucose. *Clin. Chem.*, 38(9):1613-1617.

Wu, et al. 1999. In situ electrochemical oxygen generation with an immunoisolation device. *Ann. N.Y. Acad. Sci.*, 875:105-125.

U.S. Appl. No. 09/447,227, filed Nov. 22, 1999.

U.S. Appl. No. 10/838,658 filed May 3, 2004.

U.S. Appl. No. 10/838,909 filed May 3, 2004.

U.S. Appl. No. 10/885,476 filed Jul. 6, 2004.

U.S. Appl. No. 10/896,312 filed Jul. 21, 2004.

U.S. Appl. No. 11/077,715 filed Mar. 10, 2005.

U.S. Appl. No. 11/077,883 filed Mar. 10, 2005.

U.S. Appl. No. 11/077,739 filed Mar. 10, 2005.

U.S. Appl. No. 11/077,740 filed Mar. 10, 2005.

U.S. Appl. No. 11/077,765 filed Mar. 10, 2005.

U.S. Appl. No. 11/078,230 filed Mar. 10, 2005.

U.S. Appl. No. 11/078,232 filed Mar. 10, 2005.

U.S. Appl. No. 11/077,713 filed Mar. 10, 2005.

U.S. Appl. No. 11/077,693 filed Mar. 10, 2005.

U.S. Appl. No. 11/077,714 filed Mar. 10, 2005.

U.S. Appl. No. 11/077,763 filed Mar. 10, 2005.

U.S. Appl. No. 11/077,643 filed Mar. 10, 2005.

U.S. Appl. No. 11/078,072 filed Mar. 10, 2005.

U.S. Appl. No. 11/157,746 filed Jun. 21, 2005.

U.S. Appl. No. 11/157,365 filed Jun. 21, 2005.

U.S. Appl. No. 11/158,227 filed Jun. 21, 2005.

U.S. Appl. No. 11/201,445 filed Aug. 10, 2005.

* cited by examiner

FIG. 1 – PRIOR ART

BIOINTERFACE MEMBRANE WITH MACRO-AND MICRO-ARCHITECTURE

RELATED APPLICATION

This application claims priority to U.S. Provisional Application No. 60/544,722, filed on Feb. 12, 2004, which is incorporated herein by reference in its entirety, and is hereby made a part of this specification.

FIELD OF THE INVENTION

The preferred embodiments relate generally to biointerface membranes that can be utilized with implantable devices such as devices for the detection of analyte concentrations in a biological sample (for example, from a body), cell transplantation devices, drug delivery devices, electrical signal delivering or measuring devices, and/or combinations thereof.

BACKGROUND OF THE INVENTION

Some medical devices, including implanted analyte sensors, drug delivery devices and cell transplantation devices require close vascularization and transport of solutes across the device-tissue interface for proper function. These devices generally include a biointerface membrane, which encases the device or a portion of the device to prevent access by host inflammatory cells, immune cells, or soluble factors to sensitive regions of the device.

A disadvantage of conventional implantable devices is that they often stimulate a local inflammatory response, called the foreign body response (FBR), which has long been recognized as limiting the function of implantable devices that require solute transport. The FBR has been well described in the literature.

FIG. 1 is a schematic drawing that illustrates a classical FBR to a conventional implantable device 10 implanted under the skin. There are three main layers of a FBR. The innermost FBR layer 12, adjacent to the device, is composed generally of macrophages and foreign body giant cells 14 (herein referred to as the barrier cell layer). These cells form a monolayer of closely opposed cells over the entire surface of a membrane on the implantable device. The relatively smooth surface of the membrane causes the downward tissue contracture 21 to translate directly to the cells at the device-tissue interface 26. The intermediate FBR layer 16 (herein referred to as the fibrous zone), lying distal to the first layer with respect to the device, is a wide zone (about 30-100 microns) composed primarily of fibroblasts 18, contractile fibrous tissue 20. The organization of the fibrous zone, and particularly the contractile fibrous tissue 20, contributes to the formation of the monolayer of closely opposed cells due to the contractile forces 21 around the surface of the foreign body (for example, device 10). The outermost FBR layer 22 comprises loose connective granular tissue containing new blood vessels 24.

Over time, this FBR tissue becomes muscular in nature and contracts around the foreign body so that the foreign body remains tightly encapsulated. Accordingly, the downward forces 21 press against the device-tissue interface 26, and without any counteracting forces, aid in the formation of a barrier cell layer 14 that blocks and/or refracts the transport of analytes 23 (for example, glucose) across the device-tissue interface 26.

A consistent feature of the innermost layers 12, 16 is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton and Avgoustiniatos, J. Biomech. Eng., 113:152-170 (1991).

The known art purports to increase the local vascularization in order to increase solute availability. However, it has been observed that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26. Materials or membranes employed in implantable devices are described in Brauker et al. (U.S. Pat. No. 5,741,330), Seare, Jr. (U.S. Pat. No. 5,681,572), and Picha (U.S. Pat. No. 5,564,439).

SUMMARY OF THE INVENTION

There is a need for a membrane for implantation in soft tissue that supports tissue ingrowth, interferes with and resists barrier cell layer formation, and allows the transport of analytes across the membrane long term in vivo.

Accordingly, in a first embodiment, a biointerface membrane is provided, including a macro-architecture that defines a plurality of interconnected cavities that are greater than or equal to about 20 microns in a longest dimension and a micro-architecture bonded to and/or located within at least some of the cavities of the macro-architecture, wherein the micro-architecture includes elongated strands of material that are less than or equal to about 20 microns in the shortest dimension.

In an aspect of the first embodiment, the membrane, when disposed on an implantable device, is adapted to support tissue ingrowth and to interfere with barrier cell layer formation.

In an aspect of the first embodiment, the macro-architecture is formed from homopolymer, copolymer, or terpolymer including a material selected from the group consisting of polyurethane, silicone, polyethylene-co-tetrafluoroethylene, polypropylene, polyvinylchloride, polyvinylidene fluoride, polybutylene terephthalate, polymethylmethacrylate, polyether ether ketone, cellulose ester, polysulfones, polyolefin, polyester, polycarbonate, polytetrafluoroethylene, and combinations thereof.

In an aspect of the first embodiment, the micro-architecture includes a a homopolymer, copolymer, or terpolymer including a material selected from the group consisting of polyethylene-co-tetrafluoroethylene, polyurethane, silicone, polyethylene, polypropylene, polyvinylchloride, polyvinylidene fluoride, polyvinylidene difluoride, polybutylene terephthalate, polymethylmethacrylate, polyether ether ketone, cellulose ester, polysulfones, polyolefin, nylon, polyacrylonitrile, polyesters, polycarbonates, polytetrafluoroethylene, expanded-polytetrafluoroethylene, and combinations thereof.

In an aspect of the first embodiment, the macro-architecture includes a silicone material having a structure that defines the cavities.

In an aspect of the first embodiment, the micro-architecture includes a silicone material forming the elongated strands.

In an aspect of the first embodiment, the micro-architecture includes a non-woven fibrous material.

In an aspect of the first embodiment, the micro-architecture includes expanded-polytetrafluorethylene.

In an aspect of the first embodiment, the micro-architecture is bonded to and/or located substantially throughout the cavities of the macro-architecture.

In a second embodiment, an implantable device is provided, including a device adapted to be implanted in a body and a biointerface membrane disposed on the device, the biointerface membrane including a macro-architecture that has plurality of interconnected cavities that are greater than or equal to about 20 microns in a longest dimension and a micro-architecture bonded to and/or located within at least some of the cavities of the macro-architecture, wherein the micro-architecture includes elongated strands of material that are less than or equal to about 20 microns in a shortest dimension.

In an aspect of the second embodiment, the micro-architecture is bonded to and/or located within a portion of the macro-architecture proximal to the implantable device.

In a third embodiment, an implantable glucose sensor is provided including a glucose sensor and a biointerface membrane disposed on the sensor, the biointerface membrane including a macro-architecture that has plurality of interconnected cavities that are greater than or equal to about 20 microns in a longest dimension and a micro-architecture bonded to and/or located within at least some of the cavities of the macro-architecture, wherein the micro-architecture includes elongated strands of material that are less than or equal to about 20 microns in a shortest dimension.

In a fourth embodiment, a drug-delivery device is provided including a device adapted to deliver drugs and a biointerface membrane disposed on the device, the biointerface membrane including a macro-architecture that has plurality of interconnected cavities that are greater than or equal to about 20 microns in at least one dimension and a micro-architecture bonded to and/or located within at least some of the cavities of the macro-architecture, wherein the micro-architecture includes elongated strands of material that are less than or equal to about 20 microns in a shortest dimension.

In a fifth embodiment, a cell-transplantation device is provided including cells disposed on a biointerface membrane including a macro-architecture that has plurality of interconnected cavities that are greater than or equal to about 20 microns in at least one dimension and a micro-architecture bonded to and/or located within at least some of the cavities of the macro-architecture, wherein the micro-architecture includes elongated strands of material that are less than or equal to about 20 microns in a shortest dimension.

In a sixth embodiment, a biointerface membrane is provided including a macro-architecture that has plurality of interconnected cavities that are greater than or equal to about 20 microns in at least one dimension and a micro-architecture bonded to and/or located within at least some of the cavities of the macro-architecture, wherein the micro-architecture has a nominal cavity size of less than or equal to about 20 microns.

In an aspect of the sixth embodiment, the membrane, when disposed on an implantable device, includes the macro-architecture adapted to support tissue ingrowth and to interfere with barrier cell layer formation.

In a seventh embodiment, a method for forming a biointerface membrane including a micro-architecture within a macro-architecture is provided, the method including: providing a first membrane that has a macro-architecture including co-continuous cavities and a solid portion; providing a second membrane that has a micro-architecture including a fibrous material that is less than or equal to about 20 microns in the shortest dimension; and pressing the first and second membranes together such that the second membrane at least partially exists within the cavities of the first membrane.

In an eighth embodiment, a method for forming a biointerface membrane including a micro-architecture within a macro-architecture is provided, the method including: placing a plurality of particles in a mold, wherein at least some of the particles includes a micro-architecture therein; introducing an uncured polymeric material in the mold; compressing the mold to create substantial mutual contact of adjacent particles; curing the polymeric material to form a solid interconnected matrix between the particles; and removing the particles from the matrix, whereby the matrix includes a macro-architecture that includes the micro-architecture located within at least some of the cavities.

In a ninth embodiment, a method for forming a biointerface membrane including a micro-architecture within a macro-architecture is provided, the method including: etching a first material with a micro-architecture, including etching continuous pores substantially corresponding to the micro-architecture; breaking the etched first material to form micro-porous particles of a size substantially corresponding to a desired cavity size(s) of the macro-architecture; placing a plurality of the micro-porous particles in a mold such that the particles are adjacent other particles; filling the mold with a second material, wherein the second material is a substantially uncured polymeric material; substantially solidifying the polymeric material; and selectively removing the micro-porous particles.

In an aspect of the ninth embodiment, the first material is a semi-conductor material.

In an aspect of the ninth embodiment the semi-conductor material is silicon.

In a tenth embodiment, a biointerface membrane is provided including a macro-architecture that has plurality of interconnected cavities that are greater than or equal to about 20 microns in at least one dimension and a micro-architecture that has plurality of interconnected cavities that are less than or equal to about 20 microns in at least one dimension, wherein the micro-architecture is co-continuous with and at least partially super-imposed within or bonded with a portion of the macro-architecture.

In an aspect of the tenth embodiment, the membrane including the macro-architecture supports tissue ingrowth and interferes with barrier cell layer formation.

In an eleventh embodiment, a biointerface membrane is provided including macro-architextures and microarchitectures, wherein the macro-architectures and the micro-architectures are co-continuous and interconnected, wherein the macro-architectures and the micro-architectures, when disposed on an implantable device, are adapted to promote vascularization within the biointerface membrane and to interfere with barrier cell layer formation, and wherein the biointerface membrane is configured to facilitate long-term analyte transport in vivo.

In a twelfth embodiment, a biointerface membrane is provided including a micro-architecture that includes interconnected cavities with a cavity size of less than or equal to about 20 microns in at least one dimension, and wherein the micro-architecture is co-continuous with a macro-architecture that includes interconnected cavities with a cavity size of greater than or equal to about 20 microns in at least one dimension.

In a thirteenth embodiment, a biointerface membrane is provided including a first architecture including cavities configured to facilitate ingrowth of invasive cells and vascular tissue into the biointerface membrane and a second architecture including cavities configured to facilitate ingrowth of invasive cells into the biointerface membrane while not permitting ingrowth vascular tissue.

DETAILED DESCRIPTION OF THE PREFERRED EMBODIMENT

Figure 1:
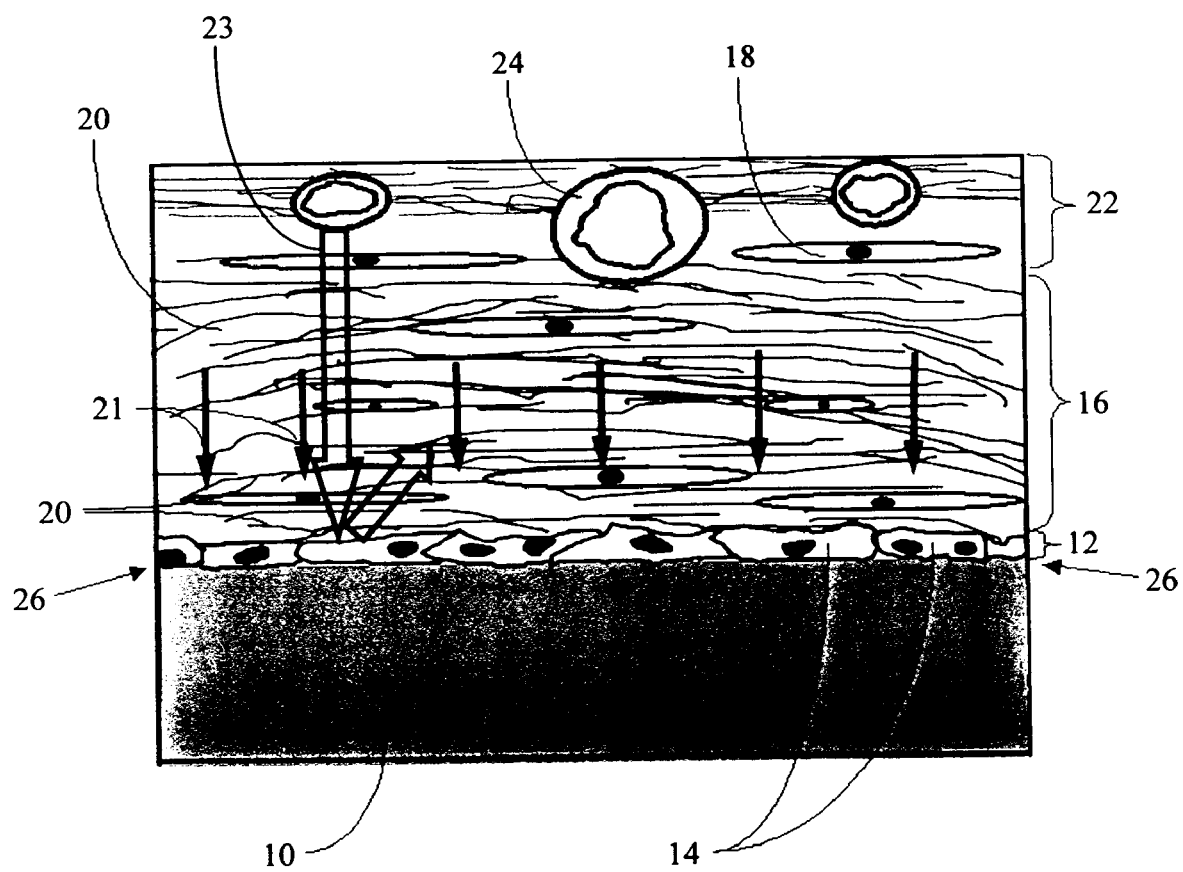
FIG. 1 is schematic diagram of a foreign body response to a conventional implantable device.

The following description and examples illustrate some embodiments of the disclosed invention in detail. Those of skill in the art will recognize that there are numerous variations and modifications of the disclosed embodiments that are encompassed by the scope of the invention. Accordingly, the description of a certain exemplary embodiment should not be deemed to limit the scope of the present invention.

DEFINITIONS

In order to facilitate an understanding of the disclosed invention, a number of terms are defined below.

The term "biointerface membrane" as used herein is a broad term and is used in its ordinary sense, including, without limitation, a permeable membrane that functions as an interface between host tissue and an implantable device. In preferred embodiments, the biointerface membrane includes macro- and micro-architectures.

The term "barrier cell layer" as used herein is a broad term and is used in its ordinary sense, including, without limita-tion, a part of a foreign body response that forms a cohesive monolayer of cells (for example, macrophages and foreign body giant cells) that substantially block the transport of molecules to the implantable device.

The term "cell processes" as used herein is a broad term and is used in its ordinary sense, including, without limitation, pseudopodia of a cell.

The term "solid portions" as used herein is a broad term and is used in its ordinary sense, including, without limitation, a material having a mechanical structure that demarcates the cavities, voids, or other non-solid portions.

The term "substantial" as used herein is a broad term and is used in its ordinary sense, including, without limitation, a sufficient amount that provides a desired function. For example, in the micro-architecture of the preferred embodiments, a sufficient number of cavities have a size that allows a sufficient number of inflammatory cells to enter therein, which can include an amount greater than 50 percent, an amount greater than 60 percent, an amount greater than 70 percent, an amount greater than 80 percent, and an amount greater than 90 percent of cavities within a preferred nominal pore size range.

The term "co-continuous" as used herein is a broad term and is used in its ordinary sense, including, without limitation, a solid portion or cavities interconnected in such a way that an unobstructed passageway is formed through at least some of the cavities and/or solid portions interconnected in such a way that that the solid portions together form a single solid structure, wherein an unbroken curved line in three dimensions can be drawn between two sides of a membrane.

The term "biostable" as used herein is a broad term and is used in its ordinary sense, including, without limitation, materials that are relatively resistant to degradation by processes that are encountered in vivo.

The term "sensor" as used herein is a broad term and is used in its ordinary sense, including, without limitation, the component or region of a device by which an analyte can be quantified.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (FT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "analyte-measuring device," as used herein is a broad term and is used in its ordinary sense, including, without limitation, any mechanism (for example, enzymatic or non-enzymatic) by which an analyte can be quantified. In one example of a glucose-measuring device, a membrane contains glucose oxidase that catalyzes the conversion of oxygen and glucose to hydrogen peroxide and gluconate:

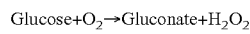

In the above reaction, for each glucose molecule consumed, there is a proportional change in the co-reactant $O_2$ and the product $H_2O_2$, one can monitor the change in either the co-reactant or the product to determine glucose concentration, such as by measuring corresponding reduction or oxidation currents at an electrochemically reactive surface.

The term "host" as used herein is a broad term and is used in its ordinary sense, including, without limitation, mammals, preferably humans.

The phrase "continuous analyte sensing" as used herein is a broad term and is used in its ordinary sense, including, without limitation, the period in which monitoring of analyte concentration is continuously, continually, and or intermittently (but regularly) performed, for example, at a rate from about every 5 seconds to about every 10 minutes.

The term "sensing region" as used herein is a broad term and is used in its ordinary sense, including, without limitation, the area of an analyte-monitoring device responsible for the detection of a particular analyte. In one example, the sensing region generally comprises a non-conductive body, a working electrode (anode), a reference electrode and a counter electrode (cathode) passing through and secured within the sensor body forming an electrochemically reactive surface at one location on the body and an electronic connective means at another location on the body, and a sensing membrane affixed to the body and covering the electrochemically reactive surface. The counter electrode has a greater electrochemically reactive surface area than the working electrode. During general operation of the sensor a biological sample (for example, blood or interstitial fluid) or a portion thereof contacts (directly or after passage through one or more membranes) an enzyme (for example, glucose oxidase); the reaction of the biological sample (or portion thereof) results in the formation of reaction products that allow a determination of the analyte (for example, glucose) level in the biological sample. In some embodiments, the sensing membrane further comprises an enzyme domain (for example, an enzyme layer), and an electrolyte phase (for example, a free-flowing liquid phase comprising an electrolyte-containing fluid described further below).

The term "electrochemically reactive surface" as used herein is a broad term and is used in its ordinary sense, including, without limitation, the surface of an electrode where an electrochemical reaction takes place. In the case of the working electrode, the hydrogen peroxide produced by the enzyme catalyzed reaction of the analyte being detected reacts creating a measurable electronic current (for example, detection of glucose utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing membrane" as used herein is a broad term and is used in its ordinary sense, including, without limitation, a permeable or semi-permeable membrane that can comprise one or more domains and constructed of materials of a few microns thickness or more, which are permeable to reactants and/or co-reactants in determining the analyte of interest. In one example, the sensing membrane comprises an immobilized glucose oxidase enzyme, which enables an electrochemical reaction with glucose and oxygen to measure a concentration of glucose.

The term, "unit cells" as used herein, is a broad term and is used in its ordinary sense, including, without limitation, the simplest polyhedron that embodies all the structural characteristics of and by repetition makes up a lattice.

The term, "lattice" as used herein, is a broad term and is used in its ordinary sense, including, without limitation, a regular geometrical arrangement of points or objects over an area or in space.

The term "proximal" as used herein, is a broad term and is used in its ordinary sense, including, without limitation, near to a point of reference such as an origin or a point of attachment.

The term "distal" as used herein, is a broad term and is used in its ordinary sense, including, without limitation, spaced relatively far from a point of reference, such as an origin or a point of attachment.

In some instances, ranges of preferred dimensions for the micro-architecture or the macro-architecture are provided. It will be appreciated that these ranges specifically encompass any dimensions at increments of 0.5 microns within the cited range. For example, the range "between about 20 microns and about 1000 microns" includes, but is not limited to, 19.0 microns or less, 19.5 microns, 20.5 microns, 21 microns 21.5 microns, 22 microns etc. through 1001 microns or more. It will also be appreciated that the provided ranges refer to preferred embodiments and that the cavity sizes of the micro-architecture and macro-architecture can be any dimensions consistent with their intended purpose.

Overview

Biointerface membranes and their use with implantable devices in a biological fluid are employed in the preferred embodiments. For example, the biointerface membranes can be utilized with implantable devices and methods for monitoring and determining analyte levels in a biological fluid, such as measurement of glucose levels for individuals having diabetes. In some embodiments, the analyte-measuring device is a continuous device, for example a subcutaneous, transdermal, or intravascular device. In some embodiments, the device can analyze a plurality of intermittent blood samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices including the described biointerface membranes and methods for their use, these biointerface membranes are not limited to use in devices that measure or monitor glucose. Rather, these biointerface membranes can be applied to a variety of devices, including for example, those that detect and quantify other analytes present in biological fluids (including, but not limited to, cholesterol, amino acids, and lactate), especially those analytes that are substrates for oxidase enzymes (U.S. Pat. No. 4,703,756, which is incorporated herein by reference in its entirety), cell transplantation devices (U.S. Pat. Nos. 6,015, 572, 5,964,745, and 6,083,523, which are incorporated herein by reference in their entirety), drug delivery devices (U.S. Pat. Nos. 5,458,631, 5,820,589, and 5,972,369, which are incorporated herein by reference in their entirety) and electrical delivery and/or measuring devices such as implantable pulse generation cardiac pacing devices (U.S. Pat. Nos. 6,157,860, 5,782,880, and 5,207,218, which are incorporated herein by reference in their entirety), electrocardiogram devices (U.S. Pat. Nos. 4,625,730 and 5,987, 352, which are incorporated herein by reference in their entirety) electrical nerve stimulating devices (U.S. Pat. Nos. 6,175,767, 6,055,456, and 4,940,065, which are incorporated herein by reference in their entirety), and in combination with angiogenic factor gene transfer technology to enhance implantable sensor function (Klueh U, Dorsky D I, Kreutzer D L. Use of vascular endothelial cell growth factor gene transfer to enhance implantable sensor function in vivo. *J Biomed Mater Res*. Dec. 15, 2003;67A(4):1072-86, which is incorporated herein by reference in its entirety), for example. One further example includes not only utilizing the biointerface membranes for transplanted cells, for example, transplanted genetically engineered cells of Langerhans, either allo, auto or xeno geneic in origin, as pancreatic beta cells to increase the diffusion of nutrients to the islets, but additionally utilizing a biointerface membrane of the preferred embodiment on a sensor proximal to the transplanted cells to sense glucose in the tissues of the patient to monitor the viability of the implanted cells.

Implantable devices for detecting analyte concentrations in a biological system can utilize the biointerface membranes of the preferred embodiments to interfere with the formation of a barrier cell layer, thereby assuring that the sensor receives analyte concentrations representative of that in the vasculature. Drug delivery devices can utilize the biointerface membranes of the preferred embodiments to protect the drug housed within the device from host inflammatory or immune cells that might potentially damage or destroy the drug. In addition, the biointerface membrane prevents or reduces the formation of a barrier cell layer that might interfere with proper dispensing of drug from the device for treatment of the host. Correspondingly, cell transplantation devices can utilize the biointerface membranes of the preferred embodiments to protect the transplanted cells from attack by the host inflammatory or immune response cells while simultaneously allowing nutrients as well as other biologically active molecules needed by the cells for survival to diffuse through the membrane.

The materials contemplated for use in preparing the biointerface membrane also eliminate or significantly delay biodegradation, which is advantageous for devices that continuously measure analyte concentrations, deliver drugs, and/or for cell transplantation devices, for example. As one example, in a glucose-measuring device, the electrochemically reactive surfaces are in contact with (or operably connected with) a thin electrolyte phase, which in turn is covered by a sensing membrane that contains an enzyme, for example, glucose oxidase, and a polymer system, such as described in U.S. Published Patent Application 2003/ 0032874, which is incorporated herein in its entirety. In this example, the biointerface membrane (which can additionally include a cell impermeable domain on one side) covers this sensing membrane and serves, in part, to protect the sensor from external forces and factors that can result in biodegradation. By significantly delaying biodegradation at the device, accurate data can be collected over long periods of time (for example, months to years). Correspondingly, biodegradation of the biointerface membrane of implantable cell transplantation devices and drug delivery devices can allow host inflammatory, immune cells, and/or immune mediators to enter these devices, thereby compromising long-term function.

Devices and probes that are implanted into subcutaneous tissue conventionally elicit a foreign body response (FBR), which forms a foreign body capsule (FBC), as part of the body's response to the introduction of a foreign material. Namely, implantation of a device (for example, a glucose sensor) results in an acute inflammatory reaction resolving to chronic inflammation with concurrent building of fibrotic tissue such as described in more detail in the background section, above. Ultimately, a mature FBC including primarily a contractile fibrous tissue forms around the device. See Shanker and Greisler, Inflammation and Biomaterials in Greco RS, ed., "Implantation Biology: The Host Response and Biomedical Devices" pp 68-80, CRC Press (1994), which is incorporated herein by reference in its entirety.

The FBC around conventional implanted devices have been shown to preclude the transport of analytes across the device-tissue interface. Thus, continuous long-term analyte transport in vivo has been conventionally believed to be unreliable or impossible. For example, because the formation of a FBC isolates an implantable sensor of the implantable device in a capsule containing fluid that does not mimic the levels of analytes (for example, glucose and oxygen) in the body's vasculature, long-term sensor function was not believed reliable. Additionally, the composition of a FBC can prevent stabilization of the implantable device, contributing to motion artifact that also renders unreliable results.

In contrast to conventional practice, it has been recognized that FBC formation is the dominant event surrounding long-term implantation of any sensor and is preferably managed or manipulated to support rather than hinder or block analyte transport. It has been observed that during the early periods following implantation of an analyte-sensing device, for example a glucose sensing device, glucose sensors can track glucose changes in vivo, although significant time delays are typically incurred. However, after a few days to two or more weeks of implantation, these devices lose their function. See, for example, U.S. Pat. No. 5,791, 344 and Gross et al. and "Performance Evaluation of the MiniMed Continuous Monitoring System During Patient home Use," Diabetes Technology and Therapeutics, (2000) 2(1):49-56, which are incorporated herein by reference in their entirety, which have reported a glucose oxidase sensor (that has been approved for use in humans by the Food and Drug Administration) that functioned well for several days following implantation but loses function quickly after 3 days. These results suggest that there is sufficient vascularization and, therefore, perfusion of oxygen and glucose to support the function of an implantable glucose sensor for the first few days following implantation. New blood vessel formation is clearly not needed for the function of a glucose oxidase mediated electrochemical sensor implanted in the subcutaneous tissue for at least several days after implantation.

After several days, however, it is believed that this lack of sensor function is most likely due to cells, such as polymorphonuclear cells and monocytes that migrate to the wound site during the first few days after implantation (for example, from the wounding of the tissue during implant). These cells consume local glucose and oxygen. If there is an overabundance of such cells, they can deplete the glucose and/or oxygen concentration before it is able to reach the sensor enzyme layer, thereby reducing the sensitivity of the device or rendering it non-functional. Further inhibition of device function may be due to inflammatory cells (for example, macrophages) that associate (for example, align at the interface) with the implantable device and physically block the transport of glucose into the device (for example, by formation of a barrier cell layer).

Additionally, these inflammatory cells can biodegrade many synthetic biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

Some methods for providing close vascularization of implantable devices using a micro-architecture without the support of a macro-architecture are described in U.S. Pat. No. 5,741,330 to Brauker et al., which is incorporated herein by reference in its entirety.

There are some advantages associated with biointerface membranes that have a micro-architecture as defined herein, for example, inducing close vascular structures, maintaining of rounded inflammatory cell morphology, preventing of barrier cell layer formation, and preventing organized fibroblasts and connective tissue from entering into the membrane. However, there are additional advantages which can result from employing biointerface membrane architectures including co-continuous interconnected macro- and micro-architectures that promote vascularization within the membrane and interfere with barrier cell layer formation, while providing a robust, biostable membrane that is suitable for long-term implantation and long-term analyte transport in vivo.

Biointerface Membranes

The biointerface membranes of the preferred embodiments include a macro-architecture and a micro-architecture, wherein the macro-architecture includes a porous structure with interconnected cavities, wherein at least some portion of the cavities are co-continuous with and at least partially filled with and/or bonded with the micro-architecture that includes a fibrous or other fine structured material that aids in preventing formation of a barrier cell layer, for example in pockets in the bottom of the cavities of the macro-architecture adjacent to the implantable device.

Figure 2:
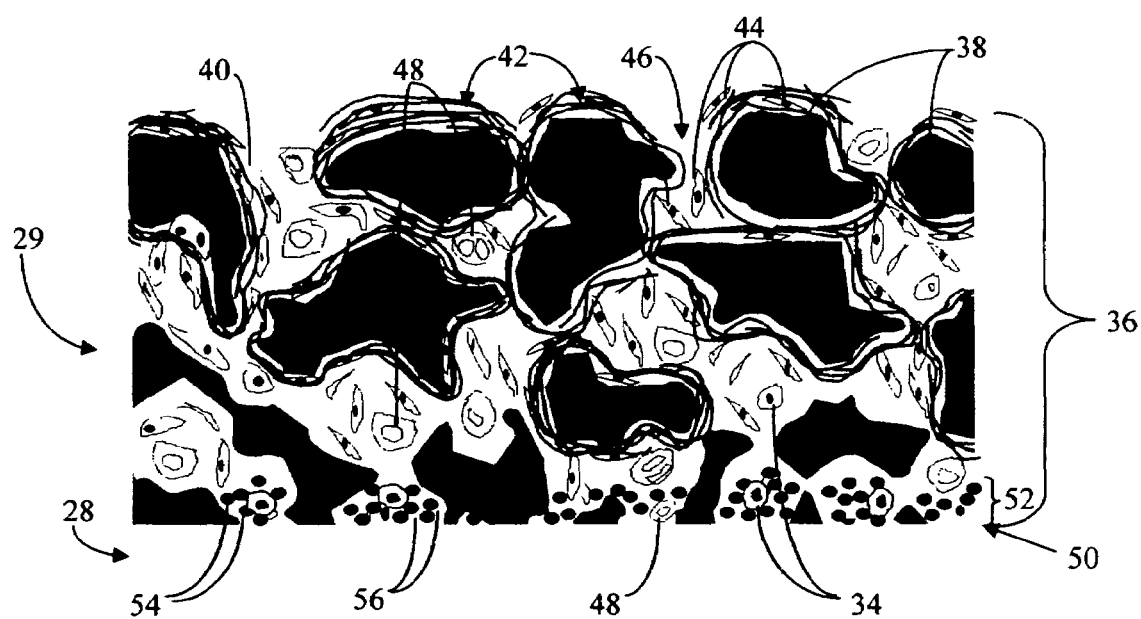
FIG. 2 is a cross-sectional schematic diagram of a foreign body response to a biointerface membrane of the preferred embodiments that includes a micro-architecture within a portion of a macro-architecture.

FIG. 2 is a cross-sectional schematic view of a biointerface membrane 29 of the preferred embodiments in vivo that has a micro-architecture 52 located within a macro-architecture 36. In some embodiments, the macro-architecture 36 includes cavities 40 and a solid portion 38, wherein the cavities 40 are between about 20 and 1000 microns in at least one dimension. In the preferred embodiment of FIG. 2, the micro-architecture 52 includes elongated strands of material that are less than about 20 microns in all but the longest dimension and/or includes a cavity or nominal pore size from about 0.6 to about 20 microns. In some embodiments, the elongated strands of material include a cavity or nominal pore size of about 1, about 3, about 5, about 7, about 9, about 11, about 13, about 15, or about 18 microns.

The macro-architecture 36 includes a solid portion 38 and a plurality of interconnected three-dimensional cavities 40 formed therein, which are described in more detail below. In general, the cavities 40 have sufficient size and structure to allow invasive cells, such as inflammatory cells (for example, macrophages 34) and blood vessels 48 to partially or completely enter into each cavity 40, and to pass through the interconnected cavities 40 toward the interface 50 of the implantable device 28. Within the cavities 40 of the macro-architecture 36, forces from the foreign body response (for example, contractile forces 42 caused by organization of the fibroblasts 44 and fibrous matrix 46) are disrupted and redirected to contract around the solid portions 38 that define the cavities 40 and away from the implantable device 28 and/or the micro-architecture 52 (see co-pending U.S. patent application Ser. No. 10/647,065, which is incorporated by reference herein in its entirety). This disruption or re-direction of the tissue contracture 42 is advantageous because the contractile forces caused by the downward tissue contracture that can otherwise cause cells to flatten against the device and occlude the transport of analytes (see FIG. 1), are instead translated to and/or counteracted by the forces that contract around the solid portions 38 (for example, throughout the interconnected cavities 40) away from the implantable device 28 and/or micro-architecture 52. Subsequently, the re-direction of the contractile tissue throughout the cavities 40 and around the solid portions 38 of the macro-architecture 36 aid in anchoring the implantable device 28 in vivo and thereby reduce motion artifact, which is known to otherwise create tissue trauma and increased foreign body response. Additionally, because the micro-architecture is substantially isolated from the downward forces of tissue contracture, the micro-architecture substantially maintains its original architecture that promotes vascularization and prevents barrier cell formation long term in vivo.

Although the macro-architecture 36 is associated with the numerous advantages described above, if used alone (for example, without a micro-architecture), some circumstances can create an opportunity for foreign body giant cells to flatten against the implantable device 28 and potentially create a layer of barrier cells that can block some or all analyte transport there across. It can therefore be advantageous to further disrupt the foreign body response, particularly in the cavities 40 proximal to the implantable device, such as described in more detail with reference to the micro-architecture, below.

The micro-architecture 52 includes a solid portion(s) 54 and a plurality of interconnected three-dimensional cavities 56 formed therein. The cavities 56 of the micro-architecture 52 have a sufficient size and structure to allow some inflammatory cells (for example, macrophages 34) to partially or completely enter therein through the cavities 56. The formation of close vascular structures 48 at the device-tissue interface 50 may be dependent on entry of some inflammatory cells (for example, macrophages 34) into the cavities 54 of the micro-architecture 52 so that the strands of the solid portion 54, which define the apertures and cavities 56, surround the cells. Thus, macrophages 34 and other inflammatory cells can grow into the micro-architecture 52, maintain a substantially rounded morphology, and stimulate blood vessels 48 to form proximal to the surface thereof. By selecting cavities of appropriate size(s), one can prevent the formation of organized fibroblasts 46 and connective tissue 42 therein, which aids in preventing barrier cell layer formation.

Although the micro-architecture 52 is associated with the numerous advantages described above, if unprotected, some circumstances can create crushing and delamination of the micro-architecture 52 which allows foreign body giant cells to flatten against the implantable device 28 and potentially create a barrier layer of cells that can block some or all analyte transport there across. It can therefore be advantageous to protect and support the micro-architecture 52 as described herein to prevent the crushing and delamination that can negate the advantageous affects of the micro-architecture 52.

Accordingly, the biointerface membranes of the preferred embodiments are designed to cover or surround at least a portion of an implantable device and combine the advantages of the micro- and macro-architectures including substantially co-continuous interconnected macro- and micro-architectures that extend from the host tissue, through the biointerface membrane, to the implantable device. Preferably, the micro-architecture is located co-continuous with and at least partially super-imposed within and/or bonded with a portion of the macro-architecture that is proximal to the implantable device and is thereby substantially protected from downward tissue contracture normally caused by a foreign body response in vivo. Additionally, the micro-architecture is substantially strengthened (supported) and protected from motion artifact and other outside influences that can otherwise negatively affect the micro-architecture if it were unprotected in vivo.

By combining the macro- and micro-architectures as described in the preferred embodiments, the combined advantages work together to manage and manipulate the high-level tissue organization and the low-level cellular organization of the foreign body response in vivo, thereby increasing neovascularization close to the device-tissue interface, preventing barrier cell layer formation, and providing good tissue anchoring, while reducing the effects of motion artifact, and disrupting the organization and/or contracture of the FBC. The result is a robust biointerface suitable for sustaining long-term analyte transport in vivo. Long-term analyte transport in vivo allows solutes (for example, oxygen, glucose and other analytes) to pass through the biointerface membrane with relative ease and reduced diffusion distance such that the implantable device can give and/or receive analytes and/or nutrients between the implant and the host.

Additionally, it is known in the art that cellular response differs depending on material characteristics such as components (for example, cavity size), architecture, and materials. Thus, while not wishing to be bound by theory it is believed that the cellular response to differing materials and architectures of some embodiments of the micro- and macro-architectures can be advantageous in influencing different types of inflammatory (for example, macrophages, monokine, leukocyte and cytokine) responses, thereby modulating the foreign body response to the implanted biointerface membrane by numerous mechanisms that can result in better wound healing (for example, good neovascularization).

Macro-Architecture

The macro-architecture 36 of the preferred embodiments includes cavities 40 and a solid portion 38, wherein the cavities are from about 20 to about 1000 microns in at least one dimension. The cavity size of the macro-architecture 36 provides a configuration and overall thickness that encourages vascular tissue ingrowth and disrupts tissue contracture that is believed to cause barrier cell formation in vivo (as indicated by the blood vessels 48 formed throughout the cavities), while providing a long-term, robust structure.

Preferably, the solid portion 38 includes homopolymers, copolymers or terpolymers of polyurethanes or silicones and, preferably, is silicone. In some alternative embodiments, the solid portion 38 can include non-woven fibers constructed of polytetrafluoroethylene, polyethylene-co-tetrafluoroethylene, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones, and block copolymers thereof including, for example, di-block, tri-block, alternating, random and graft copolymers (block copolymers are discussed in U.S. Pat. Nos. 4,803,243 and 4,686,044, hereby incorporated by reference in their entireties). Non-woven fibers that can be used include polyolefins, polyesters, polycarbonates, or polytetrafluoroethylene. However, in certain embodiments, the solid portion 38 can include other materials. Thus, it will be appreciated that the macro-architecture can be fashioned from any material suitable for the intended purpose and that the cavities therein can have any dimensions, which facilitate ingrowth of invasive cells.

Numerous methods are contemplated for manufacturing the macro-architecture 36 in order to create the preferred architecture (for example, dimensions and overall structure). In some embodiments, the macro-architecture 36 can be manufactured by forming a mold made from particles (for example, sugar, salt, or other natural or synthetic uniform or non-uniform particles), wherein the particles have shapes and sizes substantially corresponding to the desired cavity dimensions. Most often, the particles are made to coalesce or otherwise connect to provide the desired interconnectivity between the cavities 40. The desired material for the solid portion can be introduced into the mold using methods common in the art of polymer processing, for example injecting, pressing, vacuuming, depositing, or pouring. After the solid portion material is cured or solidified, the interconnected particles are then dissolved, melted, etched, or otherwise removed leaving interconnecting cavities 40 within the solid portion 38. In such embodiments, sieving can be used to determine the dimensions of the particles (which substantially correspond to the dimensions of resulting cavities). In sieving (also known as screening), the particles can be added to the sieve and then shaken to produce an "overs" and an "unders." The overs are the particles that remain on the screen and the unders are the particles that pass through the screen. Although one example of determining particle size has been described, other methods known in the art can be utilized, for example air classifiers (for example, applying opposing air flows and centrifugal forces to separate particles down to 2 microns) can be used to determine particle size when particles are smaller than 100 microns.

Accordingly in some embodiments, the dimensions of the cavities 40 can be substantially defined by the particle size used in creating the cavities. In some embodiments, the particles used to form the cavities can be substantially spherical, thus the dimensions below substantially describe a diameter of the particle and/or a diameter of the cavity 40. In some alternative embodiments, the particles used to form the cavities can be non-spherical (for example, rectangular, square, diamond, or other geometric or non-geometric shapes), thus the dimensions below substantially describe one dimension (for example, shortest, average, or longest) of the particle and/or cavity 40.

In some embodiments, a variety of different particle sizes can be used in the manufacture of the macro-architecture 36. In some embodiments, the dimensions of the particles can be somewhat smaller or larger than the dimensions of the resulting cavities due to dissolution or other precipitation that can occur during the manufacturing process, for example.

In some alternative embodiments, other molds can be used in the place of the particles described above, for example, coral, self-assembly beads, etched and broken silicon pieces, glass frit pieces, or the like. In these embodiments, the dimensions of the mold can be used to define the cavity sizes, by measuring the cavities of the final product, and/or by other measuring techniques known in the art (for example, bubble point test).

Figure 7:
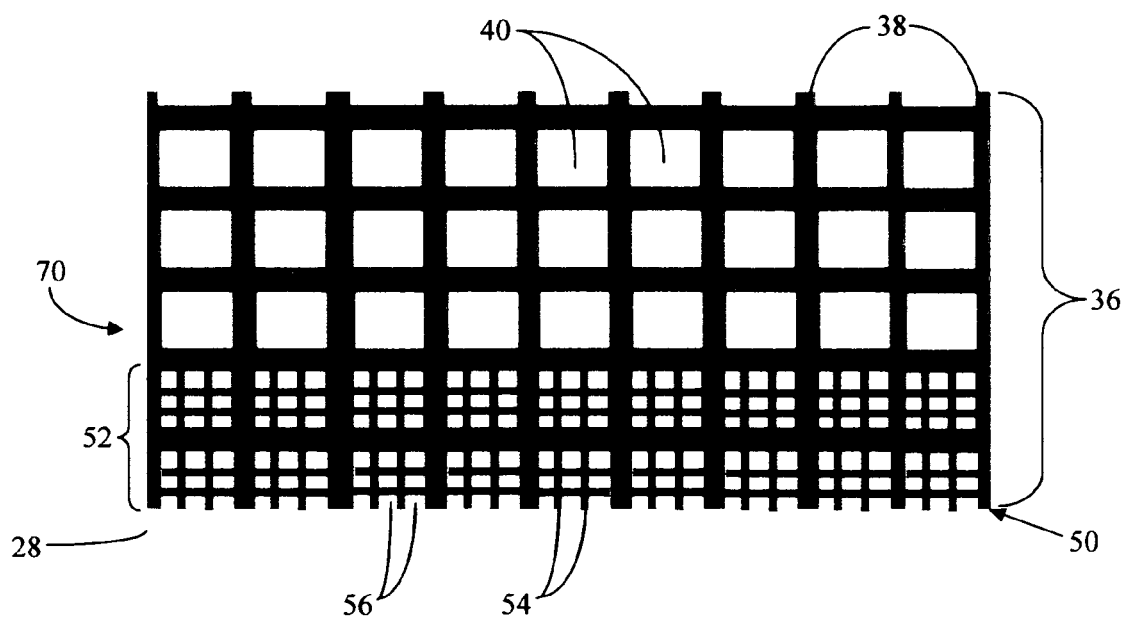
FIG. 7 is a cross-sectional schematic view of a biointerface membrane in yet another embodiment, wherein the macro- and micro-architectures are formed as a lattice structure.

In some alternative embodiments, other methods of forming three-dimensional macro-architecture can be used, for example holographic lithography, stereolithography, microstereolithography, electrochemical fabrication, microphoto-forming, spatial forming, microtransfer molding, localized electrochemical deposition, silicon micromachining, LIGA (Lithography, Electroplating, and Molding techniques), precision mechanical machining, AMANDA (combined surface micromachining, molding and diaphragm) process, or the like, wherein the cavities' sizes are defined and precisely formed by the lithographic or other such processes to form a lattice of unit cells, such as described in more detail with reference to FIG. 7, for example.

In some alternative embodiments, the macro-architecture 36 is defined using alternative methods, for example, non-woven materials, woven materials, or other such materials, such as electrospun, sintered, scattered, melt-blown, and aggregate, and are manufactured by forming the solid portions without particularly defining the cavities therebetween. Accordingly, in these alternative embodiments, structural elements that provide the three-dimensional conformation can include fibers, strands, globules, cones or rods of amorphous or uniform geometry that are smooth or rough. These elements are hereinafter referred to as "strands." In these embodiments, the solid portion of the macro-architecture includes a plurality of strands, which generally define apertures formed by a scaffold of the interconnected strands. The apertures of the material form a framework of interconnected cavities. Formed in this manner, the macro-architecture can be defined by a cavity size of about 20 to about 1000 microns in at least one dimension.

Referring still to the macro-architecture 36, a substantial number of the cavities 40, defined using any of the methods described above, are greater than or equal to about 20 microns in one dimension. In some other embodiments, a substantial number of the cavities are greater than or equal to about 30, 40, 50, 60, 70, 80, 90, 100, 120, 140, 160, 180, 200, 240, 280, 320, 360, 400, 500, 600, or 700 microns in one dimension.

In some embodiments, a substantial number of the cavities 40, defined using any of the methods described above, are less than or equal to about 1000 microns in one dimension. In other embodiments, a substantial number of the cavities are less than or equal to about 900, 800, 700, 600, 500, 400, 360, 320, 280, 240, 200, 180, 160, 140, 120, or 100 microns in one dimension.

In one alternative embodiment, wherein a substantial number of cavities 40 are greater than or equal to about 20 microns in one dimension, there can be additional cavities that are less than or equal to about 20 microns in their shortest dimension interspersed therein. In another alternative embodiment, wherein a substantial number of cavities are greater than or equal to about 20 microns in one dimension, cavity dimensions can be gradually increased or decreased progressively through the layer, including some cavities that are less than or equal to about 20 microns in one dimension.

Regarding the solid portion(s) 38 of the macro-architecture 36, a substantial number of the shortest dimensions are greater than or equal to about 5 microns and a substantial number of the longest dimensions are less than or equal to about 2000 microns in one embodiment. In other embodiments, the solid portion is less than or equal to about 10 microns in a substantial number of the shortest dimensions and less than or equal to about 1000 microns in a substantial number of the longest dimensions. In further embodiments, the solid portion is less than or equal to about 10 microns in a substantial number of the shortest dimensions and less than or equal to about 400 microns in a substantial number of the longest dimensions. However, the solid portion in other embodiments can have larger or smaller dimensions.

Micro-Architecture

The micro-architecture 52 of the preferred embodiments is preferably co-continuous with the macro-architecture and is located within at least a portion of and/or bonded to the macro-architecture 36, preferably, proximal to the implantable device 28. At least some of the cavities 56 of the micro-architecture 52 have a sufficient size and structure to allow inflammatory cells 34 to partially or completely enter therein into the cavities, however in contrast to the macro-architecture, do not allow extensive ingrowth of vascular and connective tissues 42, 44, 46 within the cavities 56. When the inflammatory cells (for example, macrophages 34) enter the cavities 56, growth of vascular structures 48 occurs proximal (for example, from about 0 to about 150 microns) to the interface 50 of the device 28 and host. The formation of close vascular structures 48 is dependent on entry of the inflammatory cells into the cavities of the micro-architecture 52 so that the solid portion surrounds the cells. Thus, the micro-architecture provides an architecture that breaks up the high level fibrous organization 42, 44, 46 of the foreign body response and encourages close vascular structures 48 in order to optimize analyte transport there across. See U.S. Pat. No. 5,741,330 to Brauker et al. and also Sanders J E, Rochefort J R. Fibrous encapsulation of single polymer microfibers depends on their vertical dimension in subcutaneous tissue. *J Biomed Mater Res*. Dec. 15, 2003; 67A(4): 1181-7. Both of the above-cited references described micro-architectures that are suitable for implementation of the micro-architecture herein, and are incorporated by reference in their entirety.

There are a variety of methods for describing and defining a micro-architecture 52 that can be used in the preferred embodiments. These methods depend, for example, on the material, its method of manufacture, and the technology available to measure the cavities and solid portion using standard techniques. A variety of materials can be useful as the micro-architecture 52 in the preferred embodiments, and thus more than one method for defining the structure can be suitable, such as described in more detail below.

In some embodiments, the micro-architecture includes non-woven materials, woven materials, or other such materials, such as electrospun, sintered, scattered, melt-blown and aggregate, which are manufactured by forming the solid portions without particularly defining the cavities therebetween. In these embodiments, for example, the solid portion 54 is formed by structural elements that provide the three-dimensional conformation, wherein solid portion 54 can be formed from fibers, strands, globules, cones or rods of amorphous or uniform geometry that are smooth or rough. These elements are hereafter referred to as "strands," and, in some embodiments, consist of a scaffold composed of strands that are less than 20 microns in all but the longest dimension. Therefore in these embodiments, the micro-architecture can be defined by a strand size of less than about 20 microns in all but the longest dimension and a sufficient number of cavities of a size and structure to allow inflammatory cells (for example, macrophages 34) to completely enter therein through the apertures that define the cavities 56, without extensive ingrowth of vascular and connective tissues therein. In these embodiments, not all of the cavities 56 need have a sufficient size to allow inflammatory cells to enter therein. What is preferred is that a sufficient number of cavities 56 have a size that allows a sufficient number of inflammatory cells to enter therein. Nor is it necessary that all of the strands 54 are less than 20 microns in all but the longest dimension. The presence of a sufficient number of strands 54 and cavities 56 of the prescribed size and architecture creates a sufficient number of vascular structures 48 proximal the device-tissue interface 50.

In some alternative embodiments, the micro-architecture can be characterized, or defined, by standard pore size tests, such as the bubble point test. In these embodiments, a micro-architecture can be selected with a nominal pore size from about 0.6 to about 20-micron nominal pore size. In some embodiments, the nominal pore size is about 1, about 3, about 5, about 7, about 9, about 11, about 13, about 15, or about 18 microns. It has been found that a porous polymer membrane having an average nominal pore size of about 0.6 to about 20 microns functions satisfactorily in creating a vascular bed within the micro-architecture 52 at the device-tissue interface 50.

The term "nominal pore size" in the context of the micro-architecture 52 in certain embodiments is derived from methods of analysis common to the membrane trade, such as the ability of the membrane to filter particles of a particular size, or the resistance of the membrane to the flow of fluids. Because of the amorphous, random and irregular nature of most of these commercially available membranes, the "nominal pore size" designation may not actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material used in the instant invention. The bubble point measurement is described, for example, in Pharmaceutical Technology May 1983 pp. 36 to 42, which is incorporated herein by reference in its entirety.

However, in some alternative embodiments, the micro-architecture of preferred embodiments can be defined by the actual size of the cavity, wherein the cavities can be formed from a mold, for example, such as described in more detail with reference to the macro-architecture, above. However, in the context of the micro-architecture it is preferable that the majority of the mold dimensions, whether particles, beads, crystals, coral, self-assembly beads, etched and broken silicon pieces, glass frit pieces, or other mold elements that form cavities, are less than about 20 microns in at least one dimension.

Accordingly in these alternative embodiments, the dimensions of the cavities 56 can be substantially defined by the mold (for example, particle size) used in creating the cavities. In some embodiments, the particles used to form the cavities can be substantially spherical, thus the dimensions below substantially describe a diameter of the particle and/or a diameter of the cavity 56. In some alternative embodiments, the particles used to form the cavities can be non-spherical (for example, rectangular, square, diamond, or other geometric or non-geometric shapes), thus the dimensions below substantially describe one dimension (for example, shortest, average, or longest) of the particle and/or cavity 56.

In some alternative embodiments, other methods of forming three-dimensional micro-architecture can be used, for example holographic lithography, stereolithography, microstereolithography, electrochemical fabrication, microphotoforming, spatial forming, microtransfer molding, localized electrochemical deposition, silicon micromachining, LIGA (Lithography, Electroplating, and Molding techniques), precision mechanical machining, AMANDA (combined surface micromachining, molding and diaphragm) process, or the like, wherein the cavities sizes are defined and precisely formed by the lithographic or other such processes to form a lattice of unit cells, such as described in more detail with reference to FIG. 7, for example.

Generally, the micro-architecture of the preferred embodiments, can be defined by the strand size, the nominal pore size, the cavity size, and/or the functional configuration that allows inflammatory cells to enter therein, while discouraging extensive ingrowth of vascular and connective tissues within the cavities 56. Therefore, the material used and its method of manufacture can dictate the definition of the micro-architecture.

The material that forms the solid portion 54 of the micro-architecture 52 can include polytetrafluoroethylene or polyethylene-co-tetrafluoroethylene. In some alternative embodiments, the solid portion includes homopolymers, copolymers or terpolymers of polyurethanes or silicones. In some embodiments, the solid portion 54 can include fibers constructed of polyethylene, polypropylene (PP), polyvinylchloride (PVC), polyvinylidene fluoride (PVDF), polyvinylidene difluoride, polybutylene terephthalate (PBT), polymethylmethacrylate (PMMA), polyether ether ketone (PEEK), polyurethanes, cellulosic polymers (for example, cellulose acetate, cellulose nitrate, mixed esters of cellulose), polysulfones, and block copolymers thereof including, for example, di-block, tri-block, alternating, random and graft copolymers (block copolymers are discussed in U.S. Pat. Nos. 4,803,243 and 4,686,044, hereby incorporated by reference). In some embodiments, the fibers 54 are comprised of polyolefins, nylon, polysulfone, and polyacrylonitrile, polyesters, polycarbonates, or polytetrafluoroethylene. However, in certain embodiments, the solid portion 54 can include other materials. In one embodiment, the solid portion 54 includes expanded-polytetrafluoroethylene (ePTFE), which is a Teflon based material. Thus, it will be appreciated that the micro-architecture can be fashioned from any material suitable for the intended purpose and that the cavities therein can have any dimensions, which allows inflammatory cells to enter therein, while discouraging extensive ingrowth of vascular and connective tissues.

Numerous methods have been contemplated for manufacturing the micro-architecture 52 in order to create the preferred architecture (for example, dimensions and overall structure). In some embodiments, the micro-architecture 52 is manufactured as an amorphous material such as described with reference to the macro-architecture 36 above, which can be modified to create the micro-architecture 52.

With regard to the overall thickness of the biointerface membrane of the preferred embodiments, the thickness can be optimized for decreased time-to-vascularize in vivo, that is, vascular tissue ingrowth can occur somewhat faster with a thinner biointerface membrane than a biointerface membrane that is relatively thicker. Decreased time-to-vascularize results in faster stabilization and functionality of the biointerface in vivo. For example in a subcutaneous implantable glucose sensor, consistent and increasing functionality of the device is at least in part a function of consistent and stable glucose transport across the biointerface membrane, which is at least in part a function of the vascularization thereof; thus quicker start-up time and/or shortened time lag (for example, the diffusion path of the glucose through the membrane can be reduced) can be accomplished by decreasing the thickness of the membrane. In general, the thickness of the biointerface membrane can be from about 20 to about 2000 microns. In some embodiments, the thickness of the biointerface membrane can be about 30, 40, 50, 60, 70, 80, 90, 100, 120, 140, 160, 180, 200, 240, 280, 320, 360, 400, 500, 600, 700, 800, 900, 1000, 1100, 1200, 1300, 1400, 1500, 1600, 1700, 1800, or about 1900 microns.

With regard to the above-described dimensions of the solid portion, the preferred structure, including the macro- and micro-architectures has been found to provide the mechanical strength and overall structural integrity to withstand the natural biological and mechanical stresses that occur long term in vivo. The optimum dimensions and overall structural integrity of the membrane will vary with the parameters of the device that it can support. For example, if the membrane is employed with a glucose sensor, the mechanical requirements of the membrane will be greater for devices having greater overall weight and surface area as compared to those that are relatively smaller.

In some embodiments, the biointerface membrane of the preferred embodiments can comprise an additional bioprotective layer, formed from the same or different material as the macro- and/or micro-architectures. The additional layer can be incorporated as a part of the biointerface membrane and lie adjacent to the implantable device or can form a part of the implantable device. In one embodiment, the bioprotective layer includes a cell impermeable domain that is impermeable to cells, and is composed of a biostable material. See U.S. Pat. No. 6,702,857, issued Mar. 9, 2004, and entitled "MEMBRANE FOR USE WITH IMPLANTABLE DEVICES," co-pending U.S. patent application Ser. No. 10/647,065, filed Aug. 22, 2003, and entitled, "POROUS MEMBRANES FOR USE WITH IMPLANTABLE DEVICES," and co-pending U.S. patent application Ser. No. 10/695,636, entitled, "SILICONE COMPOSITION FOR BIOCOMPATIBLE MEMBRANE," each of which are incorporated herein by reference in their entirety.

Design and Manufacture

The biointerface membrane of the preferred embodiments is intended to protect an implantable device from the external influences in vivo, while encouraging tissue ingrowth and allowing analyte transport. There are numerous methods of designing and manufacturing these novel biointerface membranes of the preferred embodiments, a few of which are described below.

Figure 3:
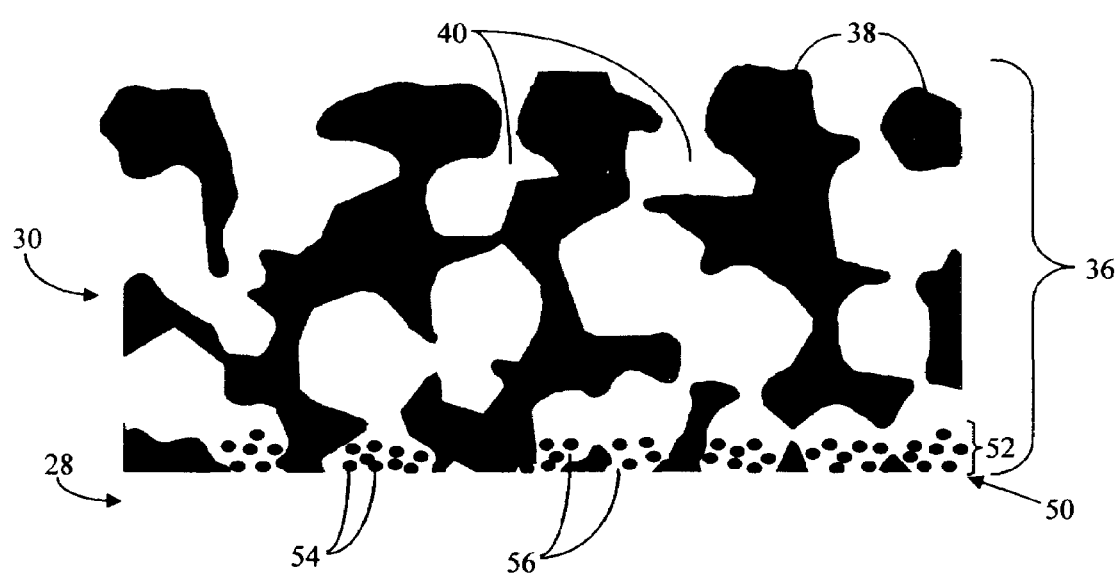
FIG. 3 is a cross-sectional schematic diagram of a biointerface membrane in one embodiment, wherein a micro-architecture is located within a portion of a macro-architecture adjacent to an implantable device.

FIG. 3 is a cross-sectional schematic view of a biointerface membrane 30 in one embodiment, wherein a micro-architecture 52 is co-continuous with and at least partially super-imposed within and/or bonded with a portion of a macro-architecture 36 proximal to an implantable device 28. The macro-architecture 36 shown in FIG. 3 is substantially amorphous, however other structures, including a uniform, regular, crystalline, lattice, reciprocal lattice, repeating unit cells, or the like, can be formed from a polymeric or non-polymeric biocompatible material (for example, silicone). In one embodiment, an amorphous structure is formed by a method such as described with reference to co-pending U.S. patent application Ser. No. 10/647,065, for example, which is incorporated herein by reference in its entirety.

In one embodiment, micro-architecture 52 is formed from a non-woven fibrous material 54, such as ePTFE, which is described with reference to U.S. Pat. No. 5,741,330 to Brauker et al., for example, which is incorporated herein by reference in its entirety. However other methods known in the art for forming the micro-architecture described herein can be used as is appreciated by one skilled in the art.

In one method of manufacturing the biointerface membrane of FIG. 3, the macro- and micro-architectures are individually formed, such as described para supra and are pressed and/or adhered together such that at least a portion of the micro-architecture 52 is disposed within the cavities 40 of the macro-architecture 36, forming a co-continuous association between the two architectures. In one alternative embodiment, pressing the micro-architecture in or on the macro-architecture during curing of the macro-architecture forms a biointerface membrane wherein the micro- and macro-architectures are co-continuous and bonded, but the micro-architecture is not necessarily disposed within the cavities of the macro-architecture. While not wishing to be bound by theory, it is believed that the co-continuous association between the macro- and micro-architectures provide for the combined advantages described in more detail above.

The resulting biointerface membrane can then be bonded (for example, cast, adhered, or otherwise chemically or mechanically bonded) to the implantable device 28, for example some or all of the solid portions of the macro-architecture 38 and/or micro-architecture 54 can be bonded to the implanted device 28. In this bonded configuration, cellular ingrowth between the implantable device 28 and the solid portions (38 and/or 54) proximal to the implantable device 28 can be significantly reduced or prevented. While not wishing to be bound by theory, it is believed that reducing or preventing cellular growth between the biointerface membrane 30 and implantable device 28 reduces or prevents delamination that can otherwise occur between the layers when cells are allowed to grow along the cavity walls.

Figure 4:
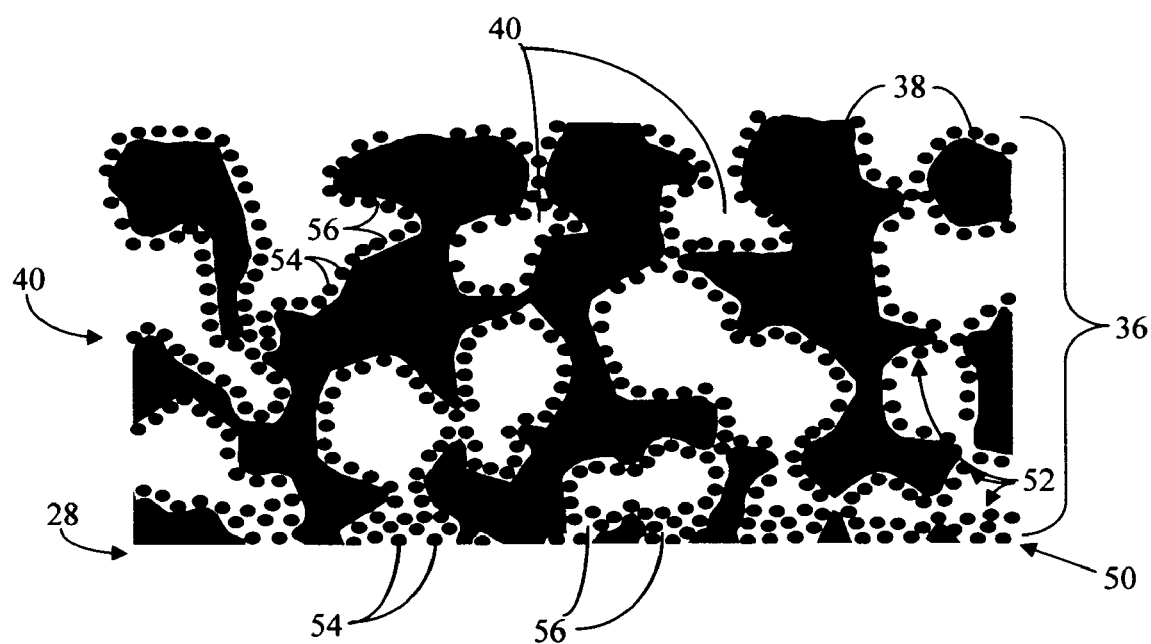
FIG. 4 is a cross-sectional schematic diagram of a biointerface membrane in another embodiment, wherein a micro-architecture is located within a macro-architecture, including along the cavity walls of the macro-architecture.

FIG. 4 is a cross-sectional schematic view of a biointerface membrane 40 in another embodiment, wherein a micro-architecture 52 is super-imposed within a macro-architecture 36, including along the walls of the cavities 40 of macro-architecture 36. The biointerface membrane 55 of this embodiment is formed from materials (for example, woven or non-woven materials) similar to those described with reference to FIG. 3, however the micro-architecture 52 extends along the walls of the cavities 40 of the macro-architecture 36 in addition to being super-imposed within the cavities 40 proximal to the implantable device 28. In some embodiments, the solid portions (38 and/or 54) can be bonded to the implantable device 28 such as describedpara supra.

In one method of manufacturing the biointerface membrane 40 of this embodiment, particles that form the mold for the cavities 40 of the macro-architecture 36 are coated with a non-woven material 54 to produce the micro-architecture 52 of the preferred embodiments, prior to pouring the polymeric material into the mold. However, other methods of producing the biointerface membrane 40 of this embodiment can be used, for example, particles can be textured or otherwise provided with the micro-architecture 52 resulting in the super-imposed structure of FIG. 4.

While not wishing to be bound by theory, it is believed that this embodiment provides the advantages described with reference to FIG. 3, and further provides a micro-architecture adjacent to cavities walls of the macro-architecture thereby preventing barrier cell layer formation thereon. In some alternative embodiments, the cavities of the macro-architecture can be fully filled with micro-architecture in some embodiments, which is believed to produce a similarly advantageous result in vivo.

Figure 5:
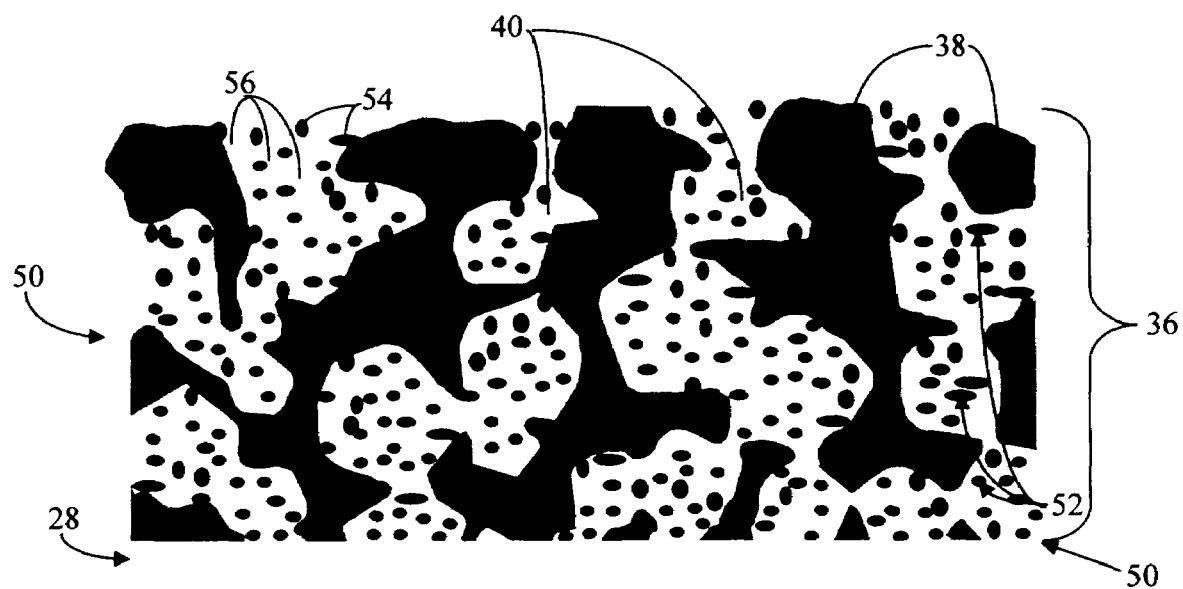
FIG. 5 is a cross-sectional schematic diagram of a biointerface membrane in yet another embodiment, wherein the micro-architecture is super-imposed within a macro-architecture, both of which can be formed by a molding process in one embodiment.

FIG. 5 is a cross-sectional schematic view of a biointerface membrane 50 in yet another embodiment, wherein a micro-architecture 52 is super-imposed within a macro-architecture 36, both of which can be formed by a molding process in some embodiments. One such embodiment uses a micro-etched three-dimensional structure as a negative, which is filled with polymer and then the negative removed using an etchant, solvent, or water, for example.

In this embodiment, a semi-conductor material, or the like, is etched with long channels creating a porous material (for example, porous silicon). The porous material can be etched to any desired architecture, including dimensions and pattern, as is appreciated by one skilled in the art. In one exemplary embodiment, bulk silicon material is etched with a micro-architecture corresponding to the desired cavity structure 56 of the micro-architecture 52 such as described in more detail elsewhere herein.

This micro-porous material is then broken to form pieces or particles of the size substantially corresponding to the desired cavity size(s) 40 of the macro-architecture 36. The particles are then optionally filtered (if necessary to obtain the proper size particles), mixed, and then pressed together to make a bed of interconnecting particles each with a sub-structure. A desired polymeric material for the solid portions 38 and 54 is then introduced into the mold using methods common in the art of polymer processing, for example injecting, pressing, vacuuming, depositing, or pouring. After curing is complete, the negative can be removed using a solvent or etchant, for example, depending on the negative mold material used. The resulting structure is schematically shown in FIG. 5, including the macro-architecture 36 with the micro-architecture 52 super-imposed therein.

Etching of bulk silicon material can be advantageous due to its relatively low cost and good reproducibility. The channels can be formed with a high aspect ratio and can extend all the way through the silicon material. The dimension and amount of negative space can be changed by optimizing the etch properties of the material. Additionally, by controlling the fabrication of the architecture (for example, via etching of semi-conductor material), the manufacture, characterization, reproducibility, and overall quality of the biointerface can be regulated and improved.

In some alternative embodiments binary solvents can be used to plate out polymeric material, and then the solvents extracted with water, or the like. The result includes cavernous micro- and/or macro-architectures with a skin on one side. This alternative embodiment can be advantageous when the material used to form the membrane allows the necessary transport of analytes therethrough. For example in an implantable glucose sensor that requires the transport of glucose and oxygen therethrough, a silicone composition such as described in co-pending U.S. patent application Ser. No. 10/695,636, which is incorporated herein by reference in its entirety, can be used to form the macro- and micro-architectures.

In some additional alternative embodiments, the macro-architecture is formed using known molding techniques such as described with reference to manufacture of the macro-architecture 36 supra, however the particles used to form the cavities 40 of the macro-architecture 36 are embedded with a fibrous material 54 such that when the particles are dissolved, the remaining fibers form the micro-structure 52 within the macro-structure 36 of the biointerface membrane 50. In one exemplary implementation, Polyethylene Terephthalate (PET) fibers are imbedded in dissolvable particles, which form the mold around which silicone is poured and cured. The resulting silicone macro-architecture 36 includes a fibrous PET micro-architecture 52 within some or all of the cavities 40 of the silicone 38.

The embodiment of FIG. 5, including micro-architecture 52 extending substantially fully through the cavities 40 of the macro-architecture 36, can be advantageous in reducing the thickness of the biointerface membrane 50, while maintaining a desired response. A decreased biointerface membrane thickness can be advantageous in decreasing the diffusion-distance and increasing time to stabilization, such as described in more detail elsewhere herein.

Figure 6:
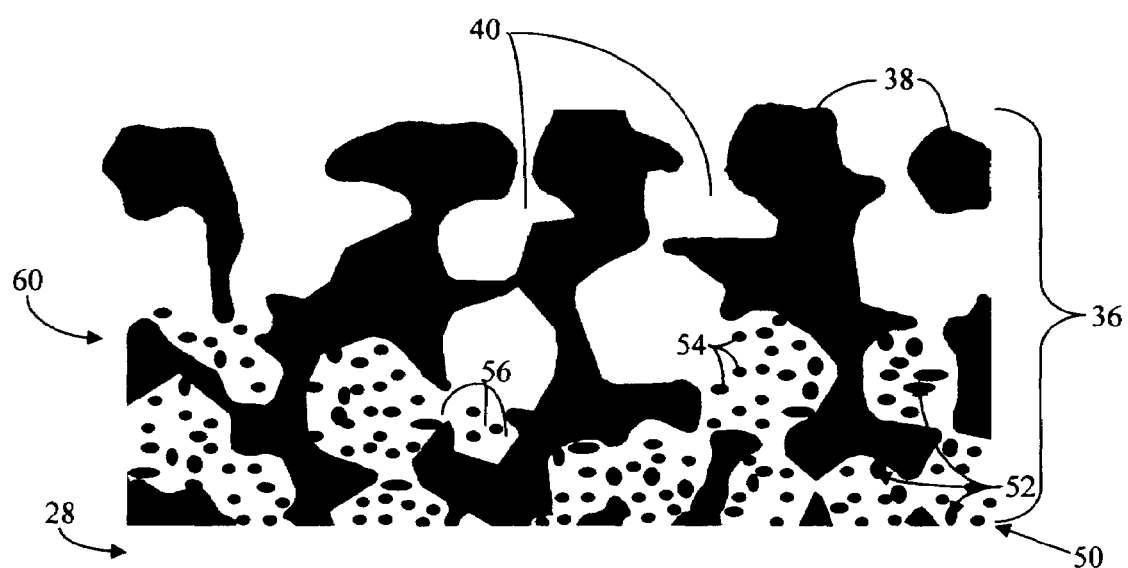
FIG. 6 is a cross-sectional schematic diagram of a biointerface membrane in yet another embodiment, wherein only a portion of the macro-architecture includes a micro-architecture super-imposed within the macro-architecture, both of which can be formed by a molding process in one embodiment.

FIG. 6 is a cross-sectional schematic view of a biointerface membrane 60 in yet another embodiment, wherein only a portion of the macro-architecture 36 has the micro-architecture 52 super-imposed therein, both of which can be formed by a molding process, such as described with reference to FIG. 5, above. The biointerface membrane 60 of this embodiment can be manufactured in a manner similar to that described above with reference to FIG. 5, however, when the particles are placed into the mold, a first layer of porous particles with a sub-structure are placed into the mold, after which a second layer of non-porous particles without a sub-structure are placed into the mold. The non-porous particles can have any structure such as described in more detail above with reference to the macro-architecture 52. Alternatively, the non-porous particles can be etched from the same material as the porous particles, including a size according the desired cavity size 40 of the macro-architecture 36, however without the porous structure.

The resulting structure is shown in FIG. 6, wherein the lower portion (for example, proximal to the implantable device 28) of the macro-architecture 36 includes micro-architecture 52 super-imposed therein, and wherein the upper portion (for example, distal to the implantable device 28) of the macro-architecture 36 does not include a micro-architecture 52 super-imposed therein. These embodiments (described with reference to FIGS. 5 and 6) utilize novel molding techniques, which provide advantageous manufacturing methods that allow the membrane to be substantially formed in one molding step and optionally directly onto an implantable device (or membrane that covers the implantable device).

FIG. 7 is a cross-sectional schematic view of a biointerface membrane in yet another embodiment, wherein the macro- and micro-architectures are formed as a lattice structure. In this embodiment, the biointerface membrane 70 illustrates the macro-architecture 36 formed from a uniform lattice of unit cells that define the cavities 40 therein and the micro-architecture 52 formed from a uniform lattice of unit cells that define the cavities 56 therein.

The unit cells that form the solid portion and interconnected cavities for both macro- and micro-architectures can be of any three dimensional shape, including, but not limited to, cube, sphere, rectangular prism, square prism, hexahedron, pyramid, hexagonal prism, octahedron, rhombicuboctahedron, dodecadodecahedron, tetrahedron, triangular pyramid, or the like. The unit cells for both the macro- and micro-architectures can have uniform, variable, or gradient dimensions.

These biointerface membranes can be manufactured using a variety of three-dimensional cutting or building techniques, such as three-dimensional holographic lithography, stereolithography, or the like. These manufacturing techniques provide a method by which the biointerface membranes can be characterized and reproduced with improved accuracy. While not wishing to be bound by theory, it is believed that precisely characterizing and reproducing the biointerface membranes of the preferred embodiments can improve the quality and control of the biointerface membranes produced.

In some alternative embodiments (not shown), the macro- and/or micro-architecture of the preferred embodiments is formed by electrospinning a polymer, such as polyurethane. This method for manufacturing non-woven fibers provides mass-producibility with controlled fiber diameter, material width and thickness. U.S. Publication No. 2003/0190383, which is incorporated herein by reference in its entirety, describes one such method. Additionally, this alternative embodiment can be advantageous in an implementation wherein the implantable device has a polymer (for example, polyurethane) outer surface on which the macro- and/or micro-architecture can directly be electrospun directly onto the implantable device.

Other alternative methods used in forming tissue engineering scaffolds can be employed with the preferred embodiments, including solvent-casting, particulate-leaching, gas foaming, fiber meshes/fiber bonding, phase separation, melt molding, emulsion freeze drying, solution casting, freeze drying, or the like. [See Sachols et al. *"Making tissue engineering scaffolds work. Review on the Application of Solid Freeform Fabrication Technology to the Production of Tissue Engineering Scaffolds"*. European Cells and Materials Vol. 5. 2003 (pp 29-400), which is incorporated herein by reference in its entirety.]

The biointerface membranes of the preferred embodiments can be implemented with a variety of implantable devices, including analyte sensors, cell transplantation devices, drug delivery devices, electrical delivery and/or measuring devices, electrocardiogram devices, or electrical nerve stimulating devices. The biointerface membranes are particularly useful in implantable devices implanted in the subcutaneous space that are concerned with the transport of analytes across the tissue-device interface, such as the examples noted above.

Figure 8A:
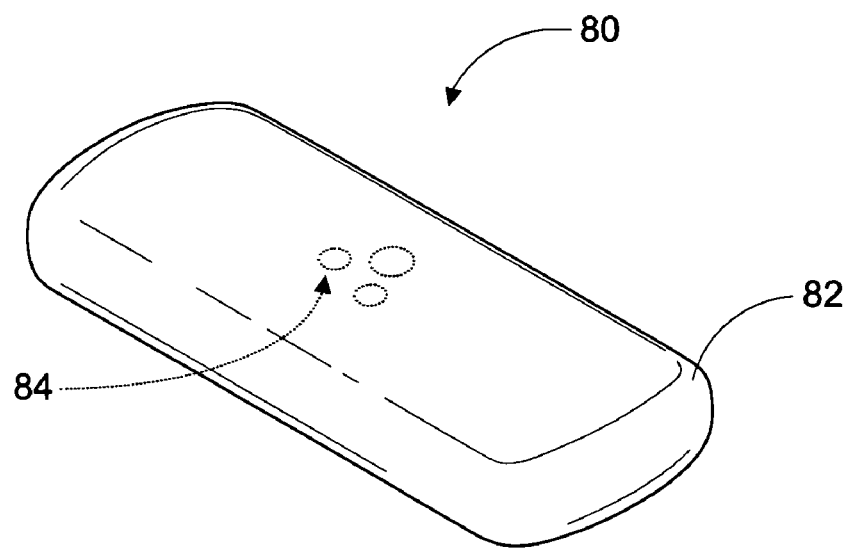
FIG. 8A is a perspective view of an assembled glucose sensor in one embodiment, including a biointerface membrane of the preferred embodiments incorporated thereon.
Figure 8B:
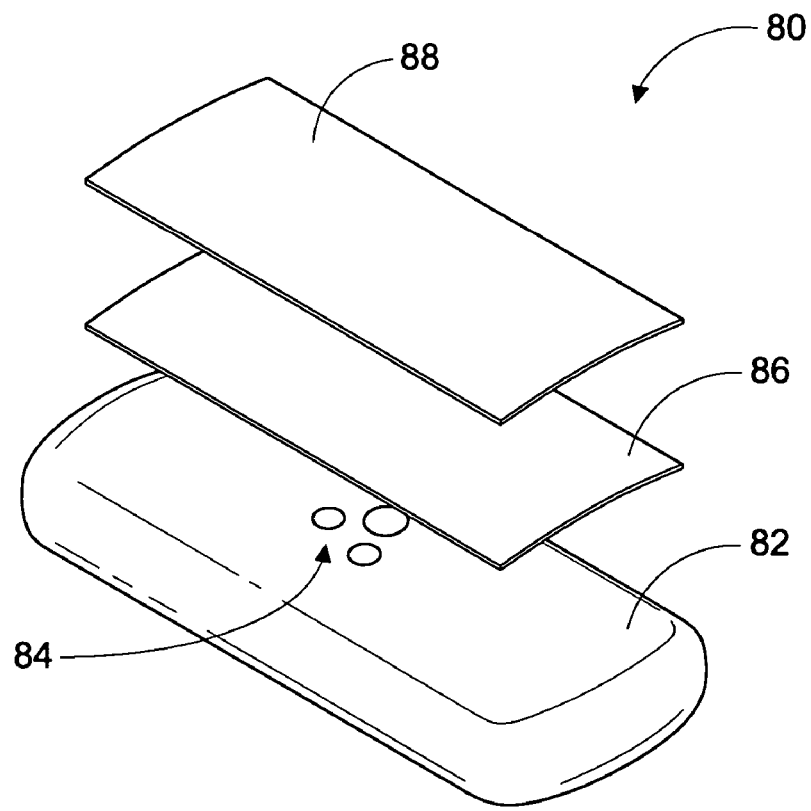
FIG. 8B is an exploded perspective view of the glucose sensor of FIG. 8A, showing the body, the sensing membrane, and the biointerface membrane of the preferred embodiments.

FIGS. 8A and 8B are perspective views of an implantable glucose sensor in one embodiment. FIG. 8A is a view of the assembled glucose sensor 80, including sensing and biointerface membranes incorporated thereon over the electrode assembly. FIG. 8B is an exploded view of the glucose sensor 80 of FIG. 8A, showing a body 82, a sensing membrane 86, and a biointerface membrane 88 of the preferred embodiments, such as described in more detail above.

The body 82 is preferably formed from epoxy molded around the sensor electronics (not shown), however the body can be formed from a variety of materials, including metals, ceramics, plastics, or composites thereof. Co-pending U.S. patent application Ser. No. 10/646,333, entitled, "Optimized Device Geometry for an Implantable Glucose Device" discloses suitable configurations suitable for the body 82, and is incorporated by reference in its entirety.

In one preferred embodiment, the sensor 80 is an enzyme-based sensor, which includes an electrode system 84 (for example, a platinum working electrode, a platinum counter electrode, and a silver/silver chloride reference electrode), which is described in more detail with reference to U.S. Publication No. 2003/0032874, which is incorporated herein by reference in its entirety. However a variety of electrode materials and configurations can be used with the implantable glucose sensor of the preferred embodiments. The top ends of the electrodes are in contact with an electrolyte phase (not shown), which is a free-flowing fluid phase disposed between a sensing membrane 86 and the electrode system 84. In this embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In this embodiment, a potentiostat is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

In some embodiments, the sensing membrane 86 includes an enzyme, for example, glucose oxidase, and covers the electrolyte phase. In one embodiment, the sensing membrane 86 generally includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane 86 modified for other devices, for example, by including fewer or additional domains, is within the scope of the preferred embodiments. Co-pending U.S. Patent Publication No. 2003.0032874, which is incorporated herein by reference in its entirety, describes membranes that can be used in some embodiments of the sensing membrane 86. In some embodiments, the sensing membrane 86 can additionally include an interference domain that blocks some interfering species; such as described in the above-cited co-pending patent application. Co-pending U.S. patent application Ser. No. 10/695,636, entitled, "SILICONE COMPOSITION FOR BIOCOMPATIBLE MEMBRANE" also describes membranes that can be used for the sensing membrane 86 of the preferred embodiments, and is incorporated herein by reference in its entirety.

The biointerface membrane 88 includes a biointerface membrane of the preferred embodiments, including macro- and micro-architectures such as described in more detail herein, which covers the sensing membrane and serves to support tissue ingrowth, interfere with the formation of a barrier cell layer, and protect the sensitive regions of the sensor 80 from host inflammatory response. While not wishing to be bound by theory, it is believed that implantable glucose sensors employing the biointerface membranes of the preferred embodiments benefit from a variety of advantages including decreased start-up time due to increased time to vascularize, decreased time lag of the analyte across the membrane, reduction or prevention of barrier cell layer formation, and reliable and constant analyte transport across the biointerface in vivo.

In one alternative embodiment, the glucose sensor comprises a needle-type sensor wherein the electrode system is in the form of an elongated needle-shaped structure. For example, the working electrode can comprise a piece of wire and the reference/counter electrode can comprise a wire (e.g., a flat wire structure) helically wound around the working electrode. An insulative layer can be placed between the working and reference/counter electrode. Those of skill in the art will appreciate other electrode structures that could be used to form a needle-shaped structure. The needle-shaped electrode system can be incorporated with one or more membranes such as described herein including a sensing membrane and a biointerface membrane of the preferred embodiments. The biointerface membrane can be deposited onto the needle-shaped electrode system or the electrode system can be inserted into a preformed biointerface membrane. For example, a biointerface membrane is contemplated with a micro-architecture disposed in a portion of a macro-architecture (periphery, center, or entire membrane), wherein the needle-type sensor is inserted into the biointerface membrane within the micro-architecture. Some examples of a needle-type sensors suitable for use with the biointerface membrane of the preferred embodiments is described in co-pending U.S. Provisional Patent Application No. 60/587,787 and U.S. Provisional Patent Application No. 60/614,683, which are incorporated herein by reference in their entirety.

The biointerface membranes described herein can also be implemented with a variety of known continuous glucose sensors, for example. In one embodiment, the biointerface membrane is implemented in conjunction with a continuous glucose sensor that comprises a subcutaneous sensor such as described with reference to U.S. Pat. No. 6,579,690 to Bonnecaze et al. and U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. All of the above patents are incorporated in their entirety herein by reference. In general, the disclosed embodiments are applicable to a variety of continuous glucose sensor configurations.

Methods and devices that are suitable for use in conjunction with aspects of the preferred embodiments are disclosed in copending U.S. application Ser. No. 10/685,636 filed Oct. 28, 2003 and entitled, "SILICONE COMPOSITION FOR BIOCOMPATIBLE MEMBRANE"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Publication No. 2003/0032874; U.S. application Ser. No. 09/447,227 filed Nov. 22, 1999 and entitled "DEVICE AND METHOD FOR DETERMINING ANALYTE LEVELS"; U.S. Publication No. 2003/0217966; and U.S. Publication No. 2004/0011671, as well as issued patents including U.S. Pat. Nos. 6,702,857; 6,741,877; 6,558,321; 6,001,067; 4,994,167; and 4,757,022. The foregoing patent applications and patents are incorporated herein by reference in their entireties, and are made a part of this specification.

All references cited herein are incorporated herein by reference in their entirety, and are made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A biointerface membrane comprising a biostable membrane configured and arranged to be disposed on an in vivo implantable device, the biostable membrane comprising:
    a macro-architecture defining a plurality of interconnected cavities that are greater than or equal to about 20 microns in a longest dimension; and
    a micro-architecture located within at least some of the cavities of the macro-architecture, wherein the micro-architecture has a plurality of interconnected cavities that are less than or equal to about 20 microns in at least one dimension, and wherein the interconnected cavities of the micro-architecture are sized such that a plurality of the interconnected cavities of the micro-architecture fit within one interconnected cavity of the macro-architecture.

2. The biointerface membrane of claim 1, wherein the membrane, when disposed on an implantable device, is adapted to support tissue ingrowth and to interfere with barrier cell layer formation.

3. The biointerface membrane of claim 1, wherein the macro-architecture is formed from a homopolymer, copolymer, or terpolymer comprising a material selected from the group consisting of polyurethane, silicone, polyethylene-co-tetrafluoroethylene, polypropylene, polyvinylchloride, polyvinylidene fluoride, polybutylene terephthalate, polymethylmethacrylate, polyether ether ketone, cellulose ester, polysulfone, polyolefin, polyester, polycarbonate, polytetrafluoroethylene, and combinations thereof.

4. The biointerface membrane of claim 1, wherein the micro-architecture comprises a homopolymer, copolymer, or terpolymer comprising a material selected from the group consisting of polyethylene-co-tetrafluoroethylene, polyurethane, silicone, polyethylene, polypropylene, polyvinylchloride, polyvinylidene fluoride, polyvinylidene difluoride, polybutylene terephthalate, polymethylmethacrylate, polyether ether ketone, cellulose ester, polysulfone, polyolefin, nylon, polyacrylonitrile, polyester, polycarbonate, polytetrafluoroethylene, expanded-polytetrafluoroethylene, and combinations thereof.

5. The biointerface membrane of claim 1, wherein the macro-architecture comprises a silicone material having a structure that defines the cavities.

6. The biointerface membrane of claim 1, wherein the micro-architecture comprises a silicone material.

7. The biointerface membrane of claim 1, wherein the micro-architecture comprises a non-woven fibrous material.

8. The biointerface membrane of claim 7, wherein the micro-architecture comprises expanded-polytetrafluoroethylene.

9. The biointerface membrane of claim 1, wherein the micro-architecture is located throughout substantially all of the cavities of the macro-architecture.

10. The biointerface membrane of claim 1, wherein the micro-architecture comprises elongated strands of material that are less than or equal to about 20 microns in a shortest dimension.

11. The biointerface membrane of claim 1, wherein the plurality of interconnected cavities of the microarchitecture are at least about 0.6 microns in the at least one dimension.

* * * * *